United States Patent
Davidson et al.

(10) Patent No.: US 12,221,452 B2
(45) Date of Patent: Feb. 11, 2025

(54) SYNTHESIS OF CANTHARIDIN

(71) Applicant: Verrica Pharmaceuticals Inc., West Chester, PA (US)

(72) Inventors: Matthew Gene Davidson, Venice, CA (US); Brian Matthew Eklov, Kalamazoo, MI (US); Peter Wuts, Kalamazoo, MI (US); Brad Melvin Loertscher, Portage, MI (US); Steven R. Schow, Redwood City, CA (US)

(73) Assignee: Verrica Pharmaceuticals Inc., West Chester, PA (US)

( * ) Notice: Subject to any disclaimer, the term of this patent is extended or adjusted under 35 U.S.C. 154(b) by 0 days.

(21) Appl. No.: 18/497,181

(22) Filed: Oct. 30, 2023

(65) Prior Publication Data
US 2024/0109911 A1    Apr. 4, 2024

Related U.S. Application Data

(63) Continuation of application No. 16/753,660, filed as application No. PCT/US2018/054373 on Oct. 4, 2018.
(Continued)

(51) Int. Cl.
     *C07D 495/22*      (2006.01)
     *C07D 333/38*      (2006.01)
     (Continued)

(52) U.S. Cl.
     CPC ......... *C07D 495/22* (2013.01); *C07D 333/38* (2013.01); *C07D 493/18* (2013.01); *C07D 495/04* (2013.01)

(58) Field of Classification Search
     CPC ..................................................... C07D 495/22
     See application file for complete search history.

(56) References Cited

U.S. PATENT DOCUMENTS

| | | |
|---|---|---|
| 600,556 A | 3/1898 | Schupphaus |
| 1,744,893 A | 1/1930 | Hein |
| (Continued) | | |

FOREIGN PATENT DOCUMENTS

| | | |
|---|---|---|
| CH | 204207 A | 4/1939 |
| CN | 1571795 A | 1/2005 |
| (Continued) | | |

OTHER PUBLICATIONS

Kadam "Single precursor for the synthesis of donor and acceptor units of the low band gap polymers: synthesis of benzodithiophene and thienopyrroledione from maleic anhydride" Tetrahedron Letters 57 (2016) 2608-2611.*

Hososmi "Chloromethyl Trimethylsilylmethyl Sulphide as a Parent Thiocarbonyl Ylide Synthon. A Simple Synthesis of Dihydro- and Tetrahydro-thiophenes" J. Chem. Soc., Chem. Commun., 1986, 1073-1074.*
Extended European Search Report, mailed Mar. 10, 2017, in connection with EP 14837297.2.
International Search Report and Written Opinion, mailed Nov. 20, 2014, in connection with PCT/US2014/052184.
International Preliminary Report on Patentability, mailed Mar. 3, 2016, in connection with PCT/US2014/052184.
Extended European Search Report, mailed Oct. 26, 2018, in connection with EP 15871116.8.
(Continued)

*Primary Examiner* — David K O'Dell
(74) *Attorney, Agent, or Firm* — Wolf, Greenfield & Sacks, P.C.

(57) ABSTRACT

The invention provides synthetic methods for the preparation of cantharidin and analogs thereof. In one aspect, the invention provides an improved Diels-Alder cycloaddition to generate a key intermediate en route to cantharidin and analogs thereof. In certain embodiments, the new Diels-Alder reaction involves reacting Compound (2) in the presence of furan, and in the absence of acid or increased pressure, in an aprotic polar solvent with slight warming, to yield Compound (1) in favorable yield and exo-endo ratio. In another aspect, the invention also provides a new Diels-Alder reaction between compounds of Formula (III) and furan to yield compounds of Formula (IV), which can then be transformed into cantharidin or analogs thereof. In yet another aspect, the invention describes a new palladium-mediated carbonylation providing another key intermediate en route to cantharidin and analogs thereof. In addition to synthetic methods, present invention also provides compounds (i.e., intermediates) useful in the synthesis of cantharidin and analogs thereof. Compounds provided herein may have biological activity, and therefore may be used in the treatment of diseases or conditions (e.g., infectious diseases and skin conditions).

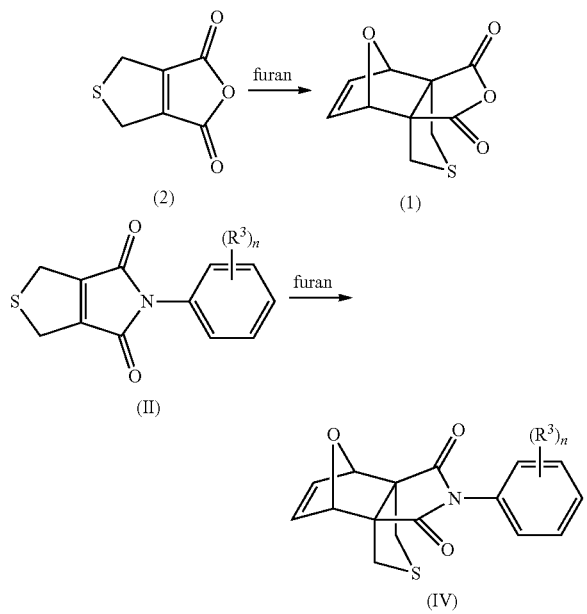

17 Claims, No Drawings

Related U.S. Application Data

(60) Provisional application No. 62/568,004, filed on Oct. 4, 2017.

(51) Int. Cl.
*C07D 493/18* (2006.01)
*C07D 495/04* (2006.01)

(56) References Cited

U.S. PATENT DOCUMENTS

| | | |
|---|---|---|
| 3,393,962 A | 7/1968 | Maurice |
| 3,981,924 A | 9/1976 | Hall |
| 4,143,050 A | 3/1979 | Rossy et al. |
| 4,148,874 A | 4/1979 | Smith |
| 4,157,967 A | 6/1979 | Meyst et al. |
| 4,298,752 A | 11/1981 | Dauben et al. |
| 4,299,006 A | 11/1981 | Cruz |
| 4,413,154 A | 11/1983 | Dessau |
| 4,895,727 A | 1/1990 | Allen |
| 5,445,462 A | 8/1995 | Johnson et al. |
| 5,464,855 A | 11/1995 | Capiris et al. |
| 5,590,780 A | 1/1997 | O'Meara |
| 5,702,694 A | 12/1997 | Chamness |
| 5,727,892 A | 3/1998 | Baudin |
| 6,066,124 A | 5/2000 | Caillouette |
| D436,661 S | 1/2001 | Berry |
| 6,379,342 B1 | 4/2002 | Levinson |
| 6,547,467 B2 | 4/2003 | Quintero |
| 6,673,031 B2 | 1/2004 | Mark |
| 6,811,342 B2 | 11/2004 | Pauchet |
| 8,518,076 B2 | 8/2013 | Stenton |
| 8,871,801 B2 | 10/2014 | Levitt |
| D771,250 S | 11/2016 | Zhang et al. |
| D772,407 S | 11/2016 | Zhang et al. |
| 9,480,691 B1 | 11/2016 | Roth |
| D801,830 S | 11/2017 | Zhang et al. |
| 10,195,635 B2 | 2/2019 | Sporrer |
| D868,160 S | 11/2019 | Lam |
| 10,745,413 B2 | 8/2020 | Davidson et al. |
| D900,312 S | 10/2020 | Davidson et al. |
| 11,052,064 B2 | 7/2021 | Davidson |
| D933,494 S | 10/2021 | Tempfli et al. |
| 11,147,790 B2 | 10/2021 | Welgus et al. |
| 11,168,091 B2 | 11/2021 | Davidson et al. |
| D938,587 S | 12/2021 | Fujii et al. |
| D947,027 S | 3/2022 | Marik |
| 11,279,165 B2 | 3/2022 | Skinner et al. |
| D957,625 S | 7/2022 | Reynolds |
| 11,559,294 B2 | 1/2023 | Pollack et al. |
| D1,036,656 S | 7/2024 | Davidson et al. |
| 2003/0068331 A1 | 4/2003 | Battaglia et al. |
| 2003/0072814 A1 | 4/2003 | Maibach et al. |
| 2004/0011830 A1 | 1/2004 | Kim |
| 2004/0152766 A1 | 8/2004 | Au-Yeung et al. |
| 2004/0162533 A1 | 8/2004 | Alley |
| 2004/0254561 A1 | 12/2004 | Stenton |
| 2005/0019418 A1 | 1/2005 | Crutchfield et al. |
| 2005/0111900 A1 | 5/2005 | Fazzolari et al. |
| 2005/0169696 A1 | 8/2005 | Albisetti |
| 2006/0110415 A1 | 5/2006 | Gupta |
| 2006/0116649 A1 | 6/2006 | Hagele |
| 2006/0180613 A1 | 8/2006 | Manesis |
| 2007/0000566 A1 | 1/2007 | Gueret |
| 2007/0111954 A1 | 5/2007 | Crutchfield et al. |
| 2007/0187437 A1 | 8/2007 | Lord |
| 2007/0233020 A1 | 10/2007 | Hearne |
| 2007/0233021 A1 | 10/2007 | Poisson et al. |
| 2007/0275045 A1 | 11/2007 | Evans et al. |
| 2008/0146674 A1 | 6/2008 | Rosenberg et al. |
| 2008/0195040 A1 | 8/2008 | Clark et al. |
| 2008/0246380 A1 | 10/2008 | Gwak |
| 2009/0110645 A1 | 4/2009 | Morelli et al. |
| 2009/0311028 A1 | 12/2009 | Odermatt et al. |
| 2011/0086109 A1 | 4/2011 | Dever |
| 2011/0208136 A1 | 8/2011 | Sollingen et al. |
| 2011/0212033 A1 | 9/2011 | Tamarkin et al. |
| 2012/0016320 A1 | 1/2012 | Lin |
| 2012/0077784 A1 | 3/2012 | Whitbourne |
| 2012/0148520 A1 | 6/2012 | Strobel et al. |
| 2012/0190658 A1 | 7/2012 | Studin |
| 2012/0312709 A1 | 12/2012 | Kaufman |
| 2013/0004230 A1 | 1/2013 | Kirk, III et al. |
| 2013/0085137 A1 | 4/2013 | Grigorian et al. |
| 2013/0197075 A1 | 8/2013 | Levitt |
| 2014/0275248 A1 | 9/2014 | Johnson |
| 2015/0118164 A1 | 4/2015 | Tamarkin et al. |
| 2015/0328259 A1 | 11/2015 | Shanler et al. |
| 2016/0193177 A1 | 7/2016 | Davidson |
| 2017/0305925 A1 | 10/2017 | Piotrowski et al. |
| 2019/0002474 A1 | 1/2019 | Davidson et al. |
| 2019/0031674 A1 | 1/2019 | Davidson et al. |
| 2020/0155498 A1 | 5/2020 | Welgus et al. |
| 2020/0270269 A1 | 8/2020 | Davidson et al. |
| 2021/0070771 A1 | 3/2021 | Davidson et al. |
| 2021/0138214 A1 | 5/2021 | Davidson et al. |
| 2021/0386703 A1 | 12/2021 | Davidson |
| 2021/0401793 A1 | 12/2021 | Welgus et al. |

FOREIGN PATENT DOCUMENTS

| | | |
|---|---|---|
| CN | 1966508 A | 5/2007 |
| CN | 101012230 A | 8/2007 |
| CN | 101108853 A | 1/2008 |
| CN | 101108854 A | 1/2008 |
| CN | 101161654 A | 4/2008 |
| CN | 101453923 A | 6/2009 |
| CN | 101798309 A | 8/2010 |
| CN | 101036774 B | 12/2010 |
| CN | 102146086 A | 8/2011 |
| CN | 102268006 A | 12/2011 |
| CN | 102336765 A | 2/2012 |
| CN | 102526146 A | 7/2012 |
| CN | 202730045 A | 2/2013 |
| CN | 202920809 U | 5/2013 |
| CN | 103923095 A | 7/2014 |
| CN | 204817029 U | 12/2015 |
| CN | 105636637 A | 6/2016 |
| CN | 106674248 A | 5/2017 |
| DE | 20016131 U1 | 11/2000 |
| EP | 0841059 A1 | 5/1998 |
| GB | 587994 A | 5/1947 |
| JP | S51-141863 A | 12/1976 |
| JP | H3-202002 A | 9/1991 |
| JP | 05-058914 A | 3/1993 |
| JP | H05-255367 A | 10/1993 |
| JP | H07-500980 A | 2/1995 |
| JP | 10-114626 A | 5/1998 |
| JP | 11-319064 A | 11/1999 |
| JP | 11-335303 A | 12/1999 |
| JP | 2001-245964 A | 9/2001 |
| JP | 2004-059446 A | 2/2004 |
| JP | 2005-187330 A | 7/2005 |
| JP | 2007-269693 A | 10/2007 |
| JP | 2008-505960 A | 2/2008 |
| JP | 2010-516410 A | 5/2010 |
| JP | 2010-235471 A | 10/2010 |
| JP | 47-39621 B2 | 8/2011 |
| JP | 2012-97152 A | 5/2012 |
| JP | 2013-507367 A | 3/2013 |
| JP | 2016-528015 A | 9/2016 |
| JP | 2017-513907 A | 6/2017 |
| KR | 10-2005-0032154 A | 4/2005 |
| KR | 100786203 B1 | 12/2007 |
| KR | 10-2016-0045086 A | 4/2016 |
| KR | 10-2017-0029413 A | 3/2017 |
| WO | WO 2008/092068 A2 | 7/2008 |
| WO | WO 2010/002476 A1 | 1/2010 |
| WO | WO 2010/079513 A2 | 7/2010 |
| WO | WO 2011/035019 A1 | 3/2011 |
| WO | WO 2012/131238 A1 | 10/2012 |
| WO | WO 2013/189841 A1 | 12/2013 |
| WO | WO 2015/027111 A1 | 2/2015 |
| WO | WO 2016/006693 A1 | 1/2016 |
| WO | WO 2016/100732 A2 | 6/2016 |

(56) References Cited

FOREIGN PATENT DOCUMENTS

| WO | WO 2016/118633 A1 | 7/2016 |
|---|---|---|
| WO | WO 2016/134130 A1 | 8/2016 |
| WO | WO 2018/226894 A1 | 12/2018 |

OTHER PUBLICATIONS

International Search Report and Written Opinion, mailed Jul. 14, 2016, in connection with PCT/US2015/066487.
International Preliminary Report on Patentability, mailed Jun. 29, 2017, in connection with PCT/US2015/066487.
Supplementary European Search Report, mailed Aug. 8, 2018, in connection with EP 16740681.8.
Extended European Search Report, mailed Dec. 4, 2018, in connection with EP 16740681.8.
International Search Report and Written Opinion, mailed Jul. 1, 2016, in connection with PCT/US2016/014139.
International Preliminary Report on Patentability, mailed Aug. 3, 2017, in connection with PCT/US2016/014139.
Extended European Search Report, mailed Feb. 2, 2021, in connection with EP 18813599.0.
Invitation to Pay Additional Fees, mailed Aug. 27, 2018, in connection with PCT/US2018/O3653.
International Search Report and Written Opinion, mailed Oct. 22, 2018, in connection with PCT/US2018/036353.
International Preliminary Report on Patentability, mailed Dec. 19, 2019, in connection with PCT/US2018/036353.
Invitation to Pay Additional Fees, mailed Sep. 20, 2018, in connection with PCT/US2018/037808.
International Search Report and Written Opinion, mailed Nov. 13, 2018, in connection with PCT/US2018/037808.
International Preliminary Report on Patentability mailed Dec. 26, 2019 in connection with International Application No. PCT/US2018/037808.
Partial Supplementary European Search Report for Application No. EP 18864069.2, mailed Apr. 12, 2021.
Extended European Search Report for Application No. EP 18864069.2, mailed Jul. 7, 2021.
Invitation to Pay Additional Fees, mailed Dec. 10, 2018, in connection with PCT/US2018/054373.
International Search Report and Written Opinion, mailed Apr. 3, 2019 in connection with PCT/US2018/054373.
International Preliminary Report on Patentability mailed Apr. 16, 2020, in connection with International Application No. PCT/US2018/054373.
[No Author Listed] CAS RN 27607-77-8. Entered STN: Nov. 16, 1984. 28 pages.
[No Author Listed] CAS RN 76262-87-8. Entered STN: Nov. 16, 1984. 19 pages.
[No Author Listed] CAS RN 89672-77-5. Entered STN: Nov. 16, 1984. 29 pages.
[No Author Listed] Journal of Organic Chemistry Author Guidelines. Last updated May 5, 2022. 3 pages.
Aitken et al., Fragmentation patterns in the gas-phase pyrolysis of some bi- and tri-cyclic sulfolanes related to the 8-thiabicyclo[4.3.0]non-3-ene 8,8-dioxide ring system . J Chem Soc. Perkin Transactions 1. 1994;16:2301-2308.
Anderson et al., Practical Process Research and Development. 1st Edition. Academic Press. Mar. 20, 2000. 81-111.
Aono et al., New method for generation of thiocarbonyl ylides from bis(trimethylsilylmethyl) sulfoxides and their application to cycloadditions. Heterocycles. 1995;40(1):249-60.
Augé et al., Catalysis by Lithium Cation: Lithium Trifluoromethanesulfonate as a Substitute for Lithium Perchlorate in Cycloadditions. Synlett 2000;6:877-9.
Bagatell, Studies On Biological Factors In Acantholysis. J Invest Dermatol. Nov. 1964;43:357-61.
Baker et al., Biotin; the structure of 2-alkyldihydrothiophene-3,4-dicarboxylic acids. J Org Chem. Jan. 1948;13(1):123-33. doi: 10.1021/jo01159a017.
Baker et al., Biotin; the structure of 2-alkyldihydrothiophene-3,4-dicarboxylic ac1449-. J Org Chem. Jan. 1948;13(1):123-33. doi: 10.1021/jo01159a017.
Bouacha et al., A theoretical study of the mechanism, stereoselectivity and Lewis acid catalyst on the Diels-Alder cycloaddition between furan and activated alkenes. Tetrahedron Letters. 2013;54:4030-4033.
Braddock et al., Stereochemistry of the Catalysed Diels-Alder Reaction between Cyclopentadiene and Dimethyl Monothionofumarate; Soft versus Hard Lewis Acids. J. Chem. Soc. Chem. Commun. Jan. 1, 1993;16:1244-6. doi: https://doi.org/10.1039/C39930001244.
Braddock et al., Stereochemistry of the Catalysed Diels-Alder Reaction between Cyclopentadiene and Dimethyl Monothionofumarate; Soft versus Hard Lewis Ac1449-. J. Chem. Soc. Chem. Commun. Jan. 1, 1993;16:1244-6. doi: https://doi.org/10.1039/C39930001244.
Brion et al., On the lewis acid catalyzed diels-alder reaction of furan. regio- and stereospecific synthesis of substituted cyclohexenols and cyclohexadienols. Tetrahedron Letters. 1982;23(50):5299-302. https://doi.org/10.1016/S0040-4039(00)85823-2.
Cacchi et al., Palladium-catalyzed carbonylation of enol triflates. A novel method for one-carbon homologation of ketones to ?,?-unsaturated carboxylic acid derivatives. Tetrahedron Letters. 26(8), 1985, pp. 1109-1112.
Chen et al., Precautions with gentian violet: skin marking made sterile, effective, and economical. Am J Infect Control. Apr. 2009;37(3):244-6. doi: 10.1016/j.ajic.2008.06.005. Epub Oct. 14, 2008.
Chung et al., Sequential Nitromethane Conjugate Addition/Elimination—PD-Catlyzed Allylation of beta-Trifloxy Acrylates. Application to Carbapenem Synthesis. Org Lett. 1999;1(11):1783-1785.
Chung et al., Sequential Nitromethane Conjugate Addition/Elimination—PD-Catalyzed Allylation of beta-Trifloxy Acrylates. Application to Carbapenem Synthesis. Org Lett. 1999;1(11):1783-1785.
Dang et al., Determination of trace cantharidin in plasma and pharmacokinetic study in beagle dogs using gas chromatography-mass spectrometry. J Anal Toxicol. Sep. 2009;33(7):384-8.
Dauben et al., Organic reactions at high pressure. Cycloadditions with furans. J. Am. Chem. Soc. 1976;98(7):1992-1993.
Dauben et al., Organic reactions at high pressure. The preparative scale synthesis of cantharidin. J. Org. Chem. 1985;50 (14):2576-2578.
Dauben et al., Simple, efficient total synthesis of cantharidin via a high-pressure Diels-Alder reaction. J. Am. Chem. Soc. 1980;102(22):6893-6894.
Earle et al., Diels-Alder reactions in ionic liqu1449-. A safe recyclable alternative to lithium perchlorate-diethyl ether mixtures. Green Chem. Feb. 1999;1:23-25. doi: 10.1039/A808052F.
Gaines et al., Trimethylgallium. In: Inorganic Syntheses. Parshall, ed. Jan. 1, 1974. Retrieved from <https://onlinelibrary.wiley.com/doi/10.1002/9780470132463.ch45> on Apr. 12, 2023. 3 pages.
Gaul, Part I. Diels-Alder reactions performed in highly polar media. Part II. Reactions of allenylstannanes with in situ generated immonium ions. Dissertation. Indiana University, Bloomington Indian, 1990. 152 pages.
Gaul, Part I. Diels-Alder reactions performed in highly polar media. Part II. Reactions of allenylstannanes with in situ generated immonium ions. Dissertation. Indiana University, Bloomington Indiana, 1990. 152 pages.
Grieco et al., Dramatic rate accelerations of Diels-Alder reactions in 5 M lithium perchlorate-diethyl ether: the cantharidin problem reexamined. J. Am. Chem. Soc. 1990;112(11):4595-4596.
Handy et al., Lithium Trifluoromethanesulfonimide in Acetone Or Diethyl-ether As a Safe Alternative To Lithium Perchlorate in Diethyl-ether for Effecting Diels-alder Reactions. Unexpected Influence of the Counterion On Exo/endo Selectivity. Synlett 1995;5:565-567.

(56) References Cited

OTHER PUBLICATIONS

Harreus et al., 2-Pyrrolidone. Ullmann's Encyclopedia of Industrial Chemistry. 2000. doi: doi: 10.1002/14356007.a22_457.pub2.
Hollis et al., Homogeneous catalysis. Titanium complex [Ti(Cp)2(CF3SO3)2] and zirconium complex [Zr(Cp)2(CF3SO3)2THF], efficient catalysts for the Diels-Alder reaction. Organometallics. Aug. 1, 1992;11(8):2745-8. https://doi.org/10.1021/om00044a004.
Hollis et al., Homogenous Catalysis: Transition Metal Based Lewis Acid Catalysts. Tetrahedron. 1993;49(25):5415-30. doi: https://doi.org/10.1016/S0040-4020(01)87259-8.
Houk et al., On Lewis Acid catalysis of diels-alder reactions. J Am Chem Soc. Jun. 13, 1973;95(12):4094-4096.
Huang, Catalysts for Hetero Diels-Alder Reaction of Imines. Chinese Journal of Organic Chemistry. Oct. 2003;23(10):1064-75.
Hubbard et al., Lewis Acid Catalyzed Diels?Alder Reactions of Highly Hindered Dienophiles. J. Org. Chem. 1998;63(12):4143-4146.
Hunt et al., Why do catalytic quantities of lewis acid generally yield more product than 1.1 equiv in the intramolecular diels-adler reaction with a furan diene? Competitive complexation NMR studies provide an answer. J Am Chem Soc. 1995;117:1049-1056.
Kharitonov et al., Synthetic transformations of higher terpeno1449-: VIII. [4+2]-Cycloaddition reactions of lambertianic acid. Russian J Organic Chem. 2003;39(1):57-74.
Kharitonov et al., Synthetic transformations of higher terpenoids: VIII. [4+2]-Cycloaddition reactions of lambertianic acid. Russian J Organic Chem. 2003;39(1):57-74.
Kronemyer et al., Verrica develops a solution for common warts. Retrieved from www.dermatologytimes.com. Nov. 13, 2017. 1 page.
Lange et al., Synthesis of 4-carboxy-2-thiabicyclo [3.2.0] Heptan-6-ones via 3-carboxy-2,3-dihydrothiophenes: potential ?-lactamase inhibitors. Tetrahedron Lett. 1985;26(15):1791-1794.
Magyarosy et al., Cycloaddition approach to the curing of polyimides via precursor containing thiophene-S,S-dioxide. Hetero Chem. 2006;17(7):648-652.
Mehdinia et al., Analysis of cantharidin in false blister beetles (Coleoptera: Oedemeridae) by headspace solid-phase microextraction and gas chromatography-mass spectrometry. J Chromatogr B Analyt Technol Biomed Life Sci. Oct. 1, 2011;879(27):2897-901. doi:10.1016/j.jchromb.2011.08.020. Epub Aug. 22, 2011.
Moed et al., Cantharidin revisited: a blistering defense of an ancient medicine. Arch Dermatol. Oct. 2001;137(10):1357-60. doi: 10.1001/archderm.137.10.1357.
Nikbakhtzadeh et al., Origin, transfer and distribution of cantharidin-related compounds in the blister beetle *Hycleus scabiosae*. J Venom Animals Toxins. 2012;18(1):88-96.
Opposition to Patent Application No. 252907 by Wavelength Enterprises, Ltd., filed Mar. 1, 2021. 78 pages.
Pagni et al., A chemical, spectroscopic, and theoretical assessment of the lewis acidity of LiClO4 in Diethyl Ether. J. Org Chem. 1993;58:3130-3133.
Prabhakar Reddy et al., Synthesis, cytotoxic activity and structure-activity relationships of hedychenone analogues. Bioorg Med Chem Lett. Apr. 15, 2010;20(8):2525-8. doi: 10.1016/j.bmcl.2010.02.101. Epub Mar. 3, 2010.
Pulce et al., Denatonium Benzoate. Human Toxicol. Jan. 1996;1-12. Accessed Sep. 12, 2022 from <https://www.sciencedirect.com/topics/medicine-and-dentistry/denatonium-benzoate>.
Rosenberg et al., Cantharidin treatment of warts at home. Arch Dermatol. Aug. 1977;113(8):1134.
Rossy et al., Aromatization of Dihydrothiophenes. Thiophenesaccharin: A Sweet Surprise. J Org Chem. 1980;45:617-620.
Rudo et al., Cantharidin—als Potenzmittel entzaubert, aber Oct. 1, 2013. Chemie in Unserer Zeit. vol. 47, Issue 5. pp. 310-316. With Supporting Information.
Schenck et al., Ausfuhrliche Mitteilung erfolgt an anderer Stelle. Naturwissenshaften Oct. 15, 1953; 40: 581.
Song et al., Ionic liqu1449—as powerful media in scandium triflate catalysed Diels-Alder reactions: significant rate acceleration, selectivity improvement and easy recycling of catalyst. Chem Commun. 2001;12:1122-3.
Song et al., Ionic liquids as powerful media in scandium triflate catalysed Diels-Alder reactions: significant rate acceleration, selectivity improvement and easy recycling of catalyst. Chem Commun. 2001;12:1122-3.
Sperry et al., Studies on the Diels-Alder reaction of annulated furans: application to the synthesis of substituted phenanthrenes. Tetrahedron Letters. Apr. 18, 2005;46(16):2789-93. Doi: 10.1016/j.tetlet.2005.02.148.
Stork et al., A Stereospecific Synthesis of Cantharidin. J. Am. Chem. Soc., 1953;75(2):384-392.
Stork et al., Cantharidin. A Stereospecific Total Synthesis. J. Am. Chem. Soc. 1951;73(9):4501-4501.
Terao et al., Thiocarbonyl Ylides. VI. New Generation of Thiocarbonyl Ylides from Organosilicon Compounds Containing Sulfur and Their 1, 3-Cycloadditions. J-Stage. 1987;35(5):1734-1740.
Torbeck et al., Cantharidin: a comprehensive review of the clinical literature. Dermatol Online J. Jun. 15, 2014;20(6):13030/qt45r512w0.
Tseng et al., Synthesis and Evaluation of Cantharidinimides on Human Cancer Cells. J Exp Clin Med. Oct. 2012;4(5):280-283.
Verma et al., Bioactive component, cantharidin from Mylabris cichorii and its antitumor activity against Ehrlich ascites carcinoma. Cell Biol Toxicol. Jun. 2012;28(3):133-47. doi: 10.1007/s10565-011-9206-6. Epub Mar. 9, 2012.
White et al., Dihydrothiophenes as precursors to fused quinolines, quinolones and coumarins via o-quinodimethane intermediates. Tetrahedron 52(9), Feb. 26, 1996, pp. 3117-3134.
White et al., Quinoline Analogues of Ortho-Quinodimethane. Tetrahedron Lett. 1995;36(33):5983-5986.
Extended European Search Report, mailed Apr. 11, 2024 for European Application No. 24153182.1.
Becerro De Bengoa Vallejo et al., Application of cantharidin and podophyllotoxin for the treatment of plantar warts. J Am Podiatr Med Assoc. Nov.-Dec. 2008;98(6):445-50. doi: 10.7547/0980445.

* cited by examiner

SYNTHESIS OF CANTHARIDIN

RELATED APPLICATIONS

This application is a continuation of and claims priority under 35 U.S.C. § 120 to U.S. Application, U.S. Ser. No. 16/753,660, filed Apr. 3, 2020, which is a national stage filing under 35 U.S.C. § 371 of international PCT application, PCT/US2018/054373, filed Oct. 4, 2018, which claims priority under 35 U.S.C. § 119 (e) to U.S. Provisional Application, U.S. Ser. No. 62/568,004, filed Oct. 4, 2017, the entire contents of each of which is incorporated herein by reference.

BACKGROUND OF THE INVENTION

Cantharidin (1,2-dimethyl-3,6-epoxyperhydrophthalic anhydride) is a lipophilic compound traditionally obtained from blister beetles, primarily of the family Meloidae. Cantharidin is an inhibitor of protein phosphatase 2A and has vesicant activity when applied to the skin. Due to its bioactivity, cantharidin is used in the treatment of various skin conditions, including the treatment of common warts and molluscum. Chemical names of cantharidin include (3aR,4S,7R,7aS)-3a,7a-dimethylhexahydro-4,7-epoxy-isobenzofuran-1,3-dione and 1,2-dimethyl-3,6-epoxyperhydrophthalic anhydride. Common names include cantharidin, cantharone, cantharidine, and kantaridin. The structure of cantharidin is shown below:

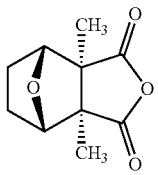

The chemical synthesis of cantharidin has proven to be challenging. Early reported syntheses are lengthy and low yielding processes, involve potentially dangerous operating conditions, and may be commercially impractical. Some cantharidin syntheses have fewer steps and improved yields but may require the use of extreme reaction conditions or dangerous reagents. Von Bruchhausen attempted the synthesis of the cantharidin in 1928. See, e.g, von Bruchhausen, F.; Bersch, II. W. *Arch. Pharm. Ber. Disch. Phurm. Ges.* 1928, 266, 697-702, which is incorporated herein by reference. His synthetic approach was based on the following retrosynthetic analysis.

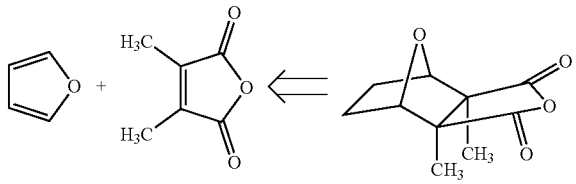

Unfortunately, the Diels-Alder reaction between the two reactants results in an equilibrium that is unfavorable with respect to the desired product. As demonstrated in the following experiment, when natural cantharidin is dehydrogenated, it spontaneously undergoes a retro Diels-Alder reaction. Studies have shown that the instability of the Diels-Alder product is due to the repulsion between the methyl groups at $C_1$ and $C_2$, and the repulsion between those methyl groups and the endo hydrogens at $C_3$ and $C_6$.

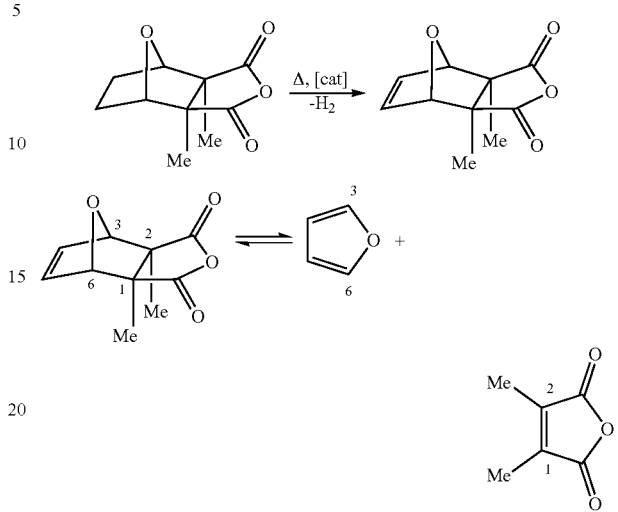

Stork published a synthesis of cantharidin in 1951 which is not economically viable. See, e.g., Stork, G.; et al. *J. Am. Chem. Soc.* 1951, 73, 4501; and Stork, G.; van Tamelen, E. E.; Friedman, L. I.; Burgstahler, A. W. *J. Am. Chem. Soc.* 1953, 75, 384; both of which are incorporated herein by reference. It is a lengthy, linear, multistep, and low-yielding process. On a large scale, this process requires the use of dangerous reagents that are both expensive and have the potential to create worker injury as well as unacceptable environmental disposal issues.

In 1953, Schenck published a Diels-Alder-based approach to cantharidin. See, e.g., Schenck, G.; Wirtz, R. *Naturwissenshaften* 1953, 40, 531, which is incorporated herein by reference. However, it still suffers from many of the issues noted above including being a long, low-yielding, linear, and multistep synthesis. Tts use on a manufacturing scale may require large-scale use of toxic bromine and disposal of an environmentally noxious brominated by-product waste stream.

In 1976, Dauben began the exploration of extreme high-pressure conditions to synthesize cantharidin. See, e.g., Dauben, W. G.; Kessel, C. R.; Takemura, K. H. *J. Am. Chem. Soc.* 1980, 102, 6893-6894; and Dauben, W. G.; Krabbenhoft, II. O. *J. Am. Chem. Soc.* 1976, 98, 1992-1993; both of which are incorporated herein by reference. This synthesis requires fewer steps to prepare cantharidin in good yield, but the extreme pressures of 4-1.5 kilobar (kbar) necessary for the Diels-Alder step may be dangerous at commercial scale of production. If done in multiple small batches, the process may be economically unattractive. This step may also require a significant capital investment in exotic hydraulic high-pressure production equipment as well as protective containment housing to ensure worker and community safety. Dauben's process is shown in the schemes below.

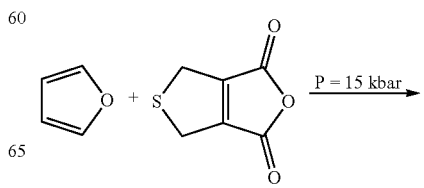

-continued

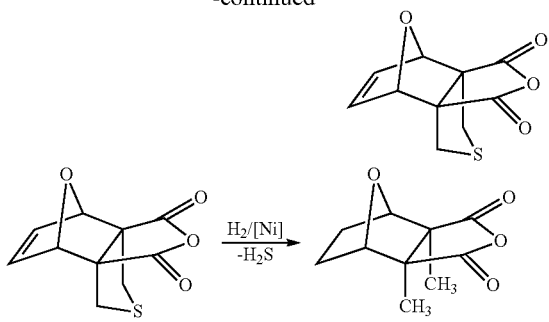

In 1990, Grieco demonstrated that the addition of 5 molar (M) lithium perchlorate in diethyl ether can facilitate the Diels-Alder reaction reported by Dauben at ambient temperatures and pressures rather than at the extreme pressures described above. See, e.g., Grieco, P. A. et al. *J. Am. Chem. Soc.* 1990, 112, 4595-4596, which is incorporated herein by reference. Unfortunately, lithium perchlorate is a high energy oxidizing agent that may form detonation-sensitive or highly explosive mixtures when combined with organic materials or metals. This includes standard reagents (Sodium), and standard plant materials (stainless steel). Accordingly, use of this procedure would significantly affect the equipment required to run this process, for instance, an entirely glass-lined reactor system, including all piping and valves. In addition, diethyl ether is a highly volatile and flammable solvent. This reaction mixture of a high energy oxidizing agent with an easily ignited solvent may be dangerous even under controlled and small-scale conditions. Additionally, perchlorate ion may be considered a significant environmental pollutant especially when released into ground water. Perchlorate may display adverse human health effects particularly targeting iodine metabolism in the thyroid. This combination of serious safety and environmental impact issues for this synthesis makes its use as a process for the commercial production of cantharidin untenable. However, the basic outline of this process for a commercial process using this short synthetic strategy remains attractive. Grieco's process is outlined in the following scheme.

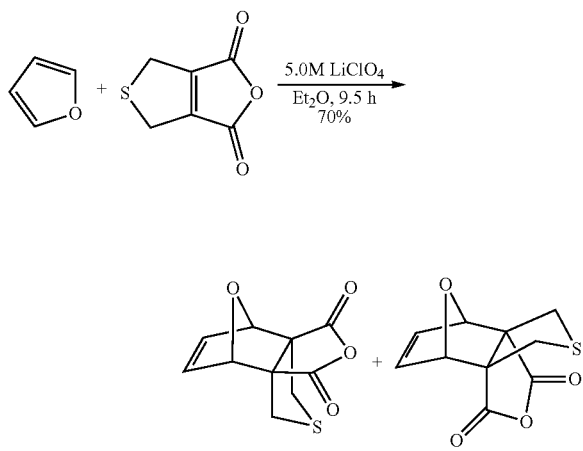

In a subsequent study by Handy in 1995, it was demonstrated that lithium trifluoromethanesulfonimide in diethyl ether or acetone also gave a good yield of Diels-Alder adduct. See, e.g., Handy, S. T.; Grieco, P. A.; Mineur, C.; Ghosez, L. *Synlett* 1995, 565-567, which is incorporated herein by reference. Unfortunately, this variant displays significant erosion in the exo-endo Diels-Alder product ratio. The exo-endo products may be difficult to separate resulting in significant losses of the desired product required for subsequent transformation to cantharidin. Such losses so late in the synthesis may adversely impact the costs of production and the ultimate profitability of the drug. Plus, the control of the increased amount of endo byproduct in the production stream may add to the regulatory and quality control burden of production as well as waste disposal costs.

Some recent developments useful in the synthesis of cantharidin and analogs thereof have been described in, e.g., International Publication No. WO 2016/100732, published Jun. 23, 2016, the entire contents of which is incorporated herein by reference.

Despite these advances in cantharidin synthesis, new methods useful in the synthesis of cantharidin and analogs thereof are needed. Preferably these methods involve mild conditions that can be used to produce on a commercial scale cantharidin, continued improvements in yield and selectivity and cantharidin analogs and derivatives that may be biologically active.

SUMMARY OF THE INVENTION

This invention relates in part to improved methods for preparing cantharidin and analogs thereof. For instance, it has been discovered that the Diels-Alder reaction of Compound (2) with furan can be carried out in the absence of increased pressure and/or in the absence of added acid (e.g, Lewis acid) to yield Compound (1) (see Scheme 1).

Scheme 1

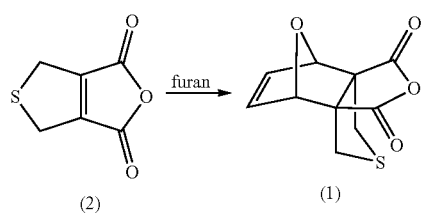

(2)　　　　　(1)

This advancement eliminates many of the disadvantages associated with previous cantharidin syntheses, including the high pressure and/or Lewis acids typically required for the key Diels-Alder step. For example, in certain embodiments, Compound (1) is formed by reacting Compound (2) with furan at atmospheric pressure, in the absence of a Lewis acid. In certain embodiments, Compound (1) is formed by reacting Compound (2) with furan at atmospheric pressure, in the absence of a Lewis acid, in a polar solvent (e.g, a polar aprotic solvent, e.g., NMP). In certain embodiments, Compound (1) is formed by reacting Compound (2) with furan at atmospheric pressure, in the absence of a Lewis acid, in a polar solvent (e.g., NMP), at a temperature above room temperature (e.g., from 40-50° C.). As discussed herein, the product of the Diels-Alder reaction, Compound (1), is useful as a key intermediate in the synthesis of cantharidin and analogs thereof.

As discussed above, provided herein are methods of preparing Compound (1):

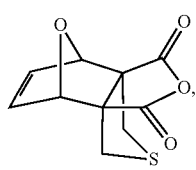

(1)

the methods comprising reacting Compound (2):

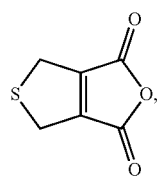

(2)

in the presence of furan; wherein the reaction is carried out in the absence of an acid (i.e., in the absence of a Lewis acid or Brønsted acid) and in the absence of increased pressure (e.g., at approximately atmospheric pressure). In certain embodiments, the reaction is carried out in the absence of a Lewis acid. In certain embodiments, the reaction is carried out in the absence of a Brønsted acid).

In certain embodiments, the Diels-Alder reaction is carried out in a solvent. In certain embodiments, the solvent is a polar solvent. In certain embodiments, the Diels-Alder reaction is carried out in an aprotic polar solvent (e.g., acetone, ethyl acetate, furan, acetonitrile, N-Methyl-2-pyrrolidone (NMP), dimethyl formamide, dimethyl acetamide, 1,3-dimethyl-2-imidazolidinone, sufolane, dimethylsulfone). In certain embodiments, the reaction is carried out at room temperature or above (e.g., between room temperature and 0.100° C., e.g., at 40-50° C.). In certain embodiments, the reaction is carried out in the absence of increased pressure (e.g., at approximately atmospheric pressure). In certain embodiments, the reaction is carried out in an aprotic polar solvent (e.g., NMP) with slight heating (e.g., at a temperature between room temperature and 100° C., e.g., at around 45° C.), and at atmospheric pressure (i.e., at approximately 1 atm).

Also provided herein are methods of preparing a compound of Formula (I), which is useful as an intermediate in the synthesis of cantharidin and analogs thereof. The method of preparing a compound of Formula (I) involves a new palladium-mediated carbonylation of a compound of Formula (II), as shown in Scheme 2.

Scheme 2

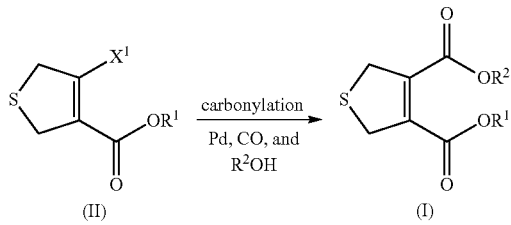

As shown in Scheme 2, provided herein are methods of preparing a compound of Formula (I):

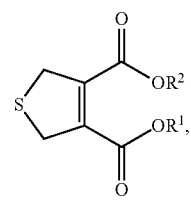

(I)

the methods comprising reacting a compound of Formula (II):

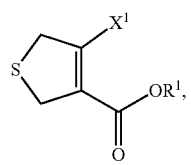

(II)

in the presence of palladium, carbon monoxide, and an alcohol of the formula $R^2OH$;

wherein:

$X^1$ is halogen, optionally substituted sulfonate, or optionally substituted phosphate;

$R^1$ and $R^2$ are independently optionally substituted alkyl, optionally substituted aryl, optionally substituted heteroaryl, optionally substituted carbocyclyl, optionally substituted heterocyclyl, or an oxygen protecting group.

The methods provided herein can be applied to the synthesis of cantharidin, for example, as shown in Scheme 3. After the Diels-Alder reaction, Compound (1) can be hydrogenated and reduced to form cantharidin. (Scheme 3). In certain embodiments, the hydrogenation and reduction are carried out in the same step.

Scheme 3

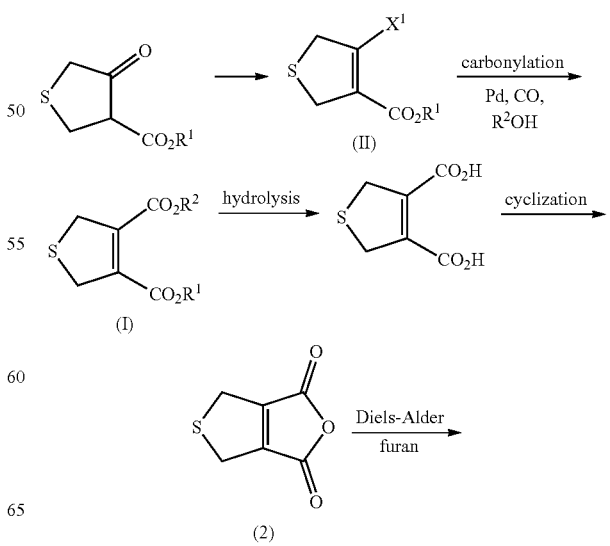

-continued

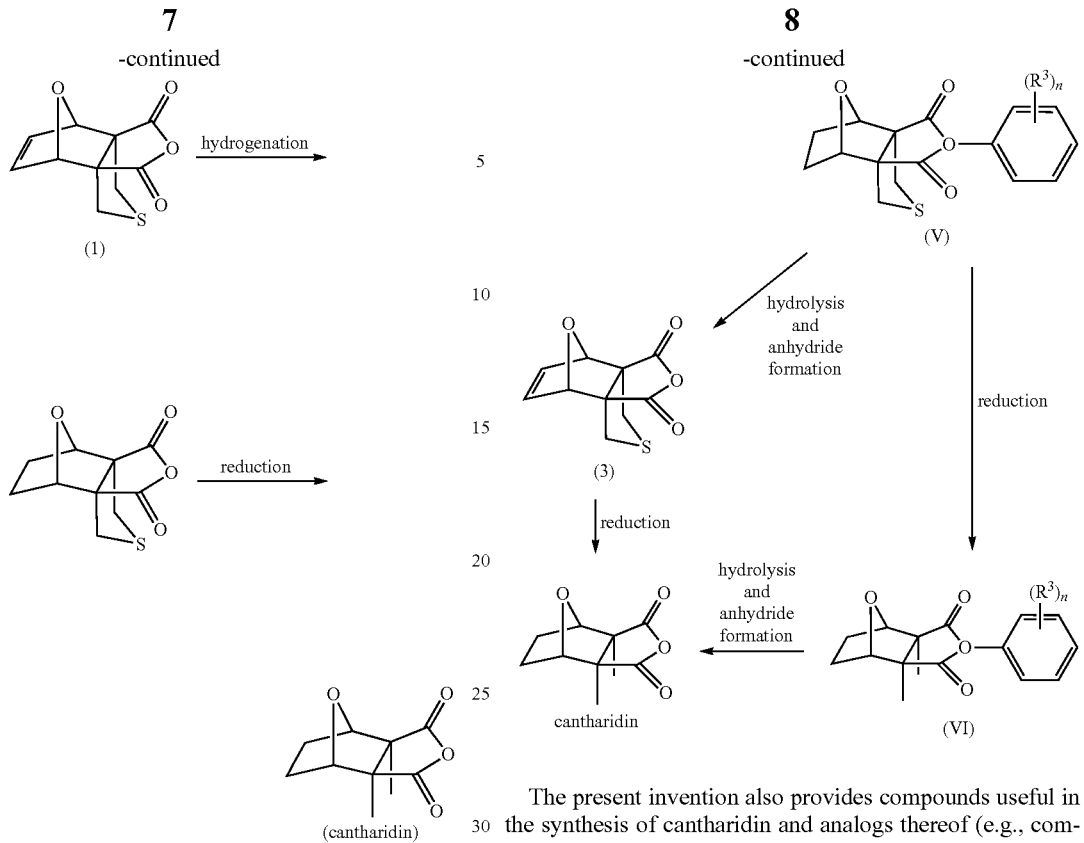

The present invention provides further methods useful in the preparation of cantharidin and analogs thereof. For example, alternative routes to cantharidin provided herein are outlined in Scheme 5. These routes also involve a new Diels-Alder reaction; in particular, a Diels-Alder reaction between a compound of Formula (III) and furan to yield a cycloadduct of Formula (IV). In certain embodiments, the Diels-Alder reaction is carried out in the absence of added acid (e.g., Lewis acid) and without the aid of increased pressure (i.e., at around atmospheric pressure). Compounds of Formula (IV) can then be hydrogenated, desulfurized, and hydrolyzed/dehydrated, in any order, to yield cantharidin.

Scheme 5

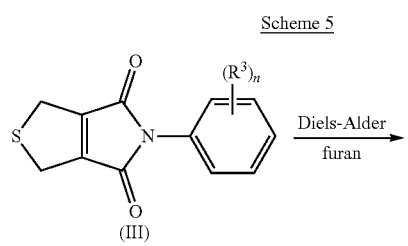

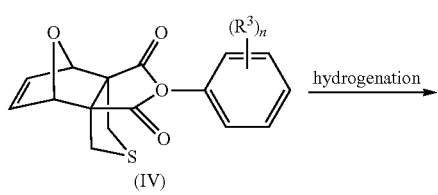

The present invention also provides compounds useful in the synthesis of cantharidin and analogs thereof (e.g., compounds of Formula (I), (II), (III), (IV), (V), and (VI)).

Synthetic intermediates provided herein may also have promising biological activity. Therefore, provided herein are pharmaceutical compositions comprising a compound of Formula (IV), (V), or (VI), or a pharmaceutically acceptable salt thereof, and a pharmaceutically acceptable excipient. Also provided herein are methods for treating a disease or condition (e.g., an infectious disease or skin condition) in a subject comprising administering to the subject a compound of Formula (IV), (V), or (VI), or a pharmaceutically acceptable salt thereof, or a pharmaceutical composition thereof. Also provided herein are uses of compounds of Formulas (IV), (V), and (VI), and pharmaceutically acceptable salts thereof, and pharmaceutical composition thereof, for the manufacture of medicaments for treating diseases or conditions (e.g., infectious diseases or skin conditions). In yet another aspect, the present invention provides kits comprising compounds or pharmaceutical compositions described herein.

The details of certain embodiments of the invention are set forth in the Detailed Description of Certain Embodiments, as described below. Other features, objects, and advantages of the invention will be apparent from the Definitions, Examples, and Claims.

DETAILED DESCRIPTION OF CERTAIN EMBODIMENTS

The present invention provides synthetic methods and intermediates useful in the synthesis of cantharidin and analogs thereof in one aspect, the present invention provides methods for the synthesis of Compound (1) using a Diels-Alder reaction between Compound (2) and furan. With respect to this reaction, the present invention provides improved conditions that provide for a safer, scalable, and/or more economical synthesis of Compound (1). In another aspect, the present invention provides methods for the preparation of compounds of Formula (I) based on a palladium-mediated carbonylation of compounds of Formula (II). Compounds of Formula (I) are useful as intermediates in the preparation cantharidin and analogs thereof. In yet another aspect, the present invention provides compounds/intermediates useful in the synthesis of cantharidin and analogs thereof.

Synthetic intermediates provided herein may also have promising biological activity, e.g., as anti-infective agents, or as agents to treat a variety of skin conditions. Therefore, provided herein are pharmaceutical compositions, methods, uses, and kits for treating a diseases or conditions.

Methods of Preparing Compound (3)

Provided herein are methods of preparing Compound (1):

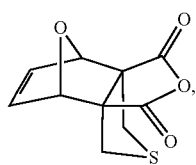

(1)

the method comprising reacting Compound (2):

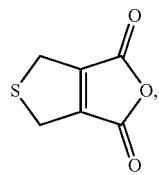

(2)

with furan;
wherein the reaction is carried out in the absence of an acid; and
wherein the reaction is carried out in the absence of increased pressure (e.g., at approximately 1 atm).

The Diels-Alder reaction described above is carried out in the absence of an acid. In certain embodiments, the reaction is carried out in the absence of added acid (i.e., no acid is added to the reaction mixture). In certain embodiments, the reaction is carried out in the absence of a Lewis acid. In certain embodiments, the reaction is carried out in the absence of an added Lewis acid or Brønsted acid. In certain embodiments, the reaction mixture consists essentially of Compound (2), furan, and solvent.

In certain embodiments, the reaction is carried out in the absence of a perchlorate. In certain embodiments, the reaction is carried out in the absence of magnesium perchlorate (Mg ClO$_4$). In certain embodiments, the reaction is carried out in the absence of lithium perchlorate (LiClO$_4$). In certain embodiments, the reaction is carried out in the absence of lithium trifluoromethanesulfonimide. In certain embodiments, the reaction is carried out in the absence of one or more Lewis acids described in International Publication No. WO 2016/100732, published Jun. 23, 2016, the entire contents of which is incorporated herein by reference.

The Diels-Alder reaction provided above is carried out in the absence of increased pressure (i.e., at approximately atmospheric pressure (1 atm)).

In certain embodiments, the reaction is carried out in a solvent. In certain embodiments, the solvent is a polar solvent. In certain embodiments, the Diels-Alder reaction is carried out in an aprotic polar solvent (e.g., acetone, ethyl acetate, tetrahydrofuran, acetonitrile. N-Methyl-2-pyrrolidone (NMP), dimethyl formamide, dimethyl acetamide, 1,3-dimethyl-2-imidazolidinone, sufolane, dimethylsulfone). In certain embodiments, the solvent is an amide, lactam, or urea such as N,N-dimethylformamide (DMF), N-methyl-2-pyrrolidone (NMP), 1,3-dimethyl-2-imidazolidinone (DMI), or 1,3-dimethyl-3,4,5,6-tetrahydro-2(1H)-pyrimidinone (DMPU). In other embodiments, the solvent is a sulfone (e.g., sufolane, dimethylsulfone). In certain embodiments, the solvent is NMP. In certain embodiments, the solvent is a co-solvent comprising NMP. Other examples of polar solvents include, but are not limited to, ketones and nitriles, such as acetone and acetonitrile. In certain embodiments, a polar solvent is selected from the group consisting of DMF, NMP, DMI, DMPU, acetone, and acetonitrile. In certain embodiments, a polar solvent is selected from the group consisting of NMP, DMPU, acetone, and acetonitrile.

In certain embodiments, the reaction is carried out in the absence of solvent. In certain embodiments, the reaction is carried out in an ionic liquid. In certain embodiments, the reaction is carried out in a ball-mill reactor.

The reaction can be carried out at any concentration of the reactants in solvent or reaction mixture. In certain embodiments, the concentration of Compound (2) in solvent or reaction mixture is approximately 0.0.1 molar (mol/L, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, 10 M. In certain embodiments, the reaction is carried out at a concentration of 1-20 M in solution with respect to Compound (2). In certain embodiments, the concentration is 5-15 M. In certain embodiments, the concentration is 10-15 M.

The reaction may be carried out at any temperature. The reaction temperature may be approximately 20° C., 30° C., 40° C., 50° C., 60° C., 70° C. 80° C., 90° C., 100° C., 1.10° C., 120° C., 130° C., 140° C., or 150° C. in certain embodiments, the reaction temperature is above 100° C. In certain embodiments, the reaction is carried out at a temperature below 100° C. In certain embodiments, the reaction is carried out at a temperature above room temperature (21° C. or 70° F.). In certain embodiments, the temperature is between room temperature and 100° C. In certain embodiments, the reaction is carried out at a temperature between 30 and 60° C. In certain embodiments, the reaction is carried out at a temperature between 40 and 50° C. In certain embodiments, the reaction is carried out at approximately 40° C., 41° C., 42° C., 43° C., 44° C., 45° C., 46° C., 47° C., 48° C., 49° C., or 50° C. In certain embodiments, the reaction is carried out at around 45° C.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

The reaction mixture may contain any ratio of the reactants, specifically, Compound (2) and furan. In certain embodiments, furan is present in greater than 1 equivalent relative to the amount of Compound (2) in the reaction mixture (i.e., excess). In certain embodiments, the ratio of. Compound (2) to furan in the reaction mixture is from 1:1 to 1:20. In certain embodiments, the ratio of Compound (2)

to furan in the reaction mixture is from 1:1 to 1:10. In certain embodiments, the ratio of Compound (2) to furan in the reaction mixture is approximately 1:2, 1:3, 1:4, 0.1:5, 1:6, 0.1:7, 1:8, 1:9, 1:10, 1:11, 1:12, 1:13, 1:14, 1:15, 1:16, 1:17, 1:18, 1:19, or 1:20. In certain embodiments, the ratio of Compound (2) to furan in the reaction mixture is from 1:4 to 1:5. In certain embodiments, the ratio of Compound (2) to furan in the reaction mixture is about 1:4.1, 1:4.2, 1:4.3, 1:4.4, 1:4.5, 1:4.6, 1:4.7, 1:4.8, or 1:4.9.

As described herein, the reaction may be carried out in the absence of added acid (e.g., Lewis and/or Brønsted acids) at approximately 1 atm. In some instances, the reaction solvent and temperature may be varied as follows. In certain embodiments, the reaction is carried out in a polar solvent at room temperature or above. In certain embodiments, the reaction is carried out in a polar solvent between room temperature and 100° C. In certain embodiments, the reaction is carried out in a polar solvent at elevated temperature (i.e., above room temperature). In certain embodiments, the reaction is carried out in a polar solvent at a temperature between room temperature and 100° C. In certain embodiments, the reaction is carried out in a polar solvent at a temperature between 30° C. and 100° C. In certain embodiments, the reaction is carried out in a polar solvent at a temperature between 30° C. and 60° C. in certain embodiments, the reaction is carried out in a polar solvent at a temperature between 40° C. and 50° C. In certain embodiments, the reaction is carried out in a polar solvent at a temperature around 50° C. In certain embodiments, the reaction is carried out in a polar solvent at a temperature around 45° C. In certain embodiments, the reaction is carried out in a polar solvent at a temperature around 40° C. In certain embodiments, the reaction is carried out in NMP at room temperature or above. In certain embodiments, the reaction is carried out in NMP at between room temperature and 100° C. In certain embodiments, the reaction is carried out in NMP at elevated temperature (i.e., above room temperature). In certain embodiments, the reaction is carried out in NMP at a temperature between room temperature and 100° C. In certain embodiments, the reaction is carried out in NMP at a temperature between 30° C. and 100° C. In certain embodiments, the reaction is carried out in NMP at a temperature between 30° C. and 60° C. In certain embodiments, the reaction is carried out in NMP at a temperature between 40° C. and 50° C. In certain embodiments, the reaction is carried out in NMP at a temperature around 50° C. In certain embodiments, the reaction is carried out in NMP at a temperature around 45° C. In certain embodiments, the reaction is carried out in NMP at a temperature around 40° C.

In the methods provided herein, Compound (1) can be formed as the exo or endo cycloadduct, or as a mixture of exo and endo cycloadducts. The "exo" and "endo" adducts are shown below:

exo

-continued

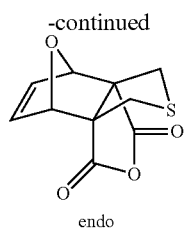
endo

For cantharidin, a high exo-to-endo ratio is desired. In certain embodiments, the Diels-Alder methods provided herein yield a favorable exo-to-endo ratio. For instance, the exo-to-endo product ratios produced by methods disclosed herein can be at least about 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or 100:0. The percentage of exo product per total amount of product can be at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 99.99%, 99.999%, or 100%. In certain embodiments, the exo/endo ratio is from about 70:30 to 99:1. In certain embodiments, the exo/endo ratio is from about 70:30 to 90:10. In certain embodiments, the exo/endo ratio is from about 70:30 to 80:20. In certain embodiments, the exo/endo ratio is about 70:30, 71:29, 72:28, 73:27, 74:26, 75:25, 76:24, 77:23, 78:22, 79:21, or 80:20, in certain embodiments, the exo/endo ratio is about 75:25. In certain embodiments, the exo/endo ratio is from about 80:20 to about 90:10. In certain embodiments, the exo/endo ratio is about 80:20. In certain embodiments, the exo/endo ratio is about 81:19. In certain embodiments, the exo/endo ratio is about 82:18. In certain embodiments, the exo/endo ratio is about 83:17. In certain embodiments, the exo/endo ratio is about 84:16. In certain embodiments, the exo/endo ratio is about 85:15. In certain embodiments, the exo/endo ratio is about 86:14. In certain embodiments, the exo/endo ratio is about 87:13. In certain embodiments, the exo/endo ratio is about 88:12. In certain embodiments, the exo/endo ratio is about 89:11. In certain embodiments, the exo/endo ratio is about 90:10. In certain embodiments, the exo/endo ratio is about 95:5. In certain embodiments, the exo/endo ratio is about 98:2. In certain embodiments, the exo/endo ratio is about 99:1. In certain embodiments, the exo/endo ratio is about 99.10:0.10.

Any of these exo/endo ratios can be achieved by, in certain embodiments, reacting Compound (2) with furan in the absence of added acid, at approximately atmospheric pressure, in an aprotic polar solvent (e.g., NMP), with heating above room temperature (e.g., between room temperature and 100° C., e.g., between 40 and 50'C). In certain embodiments, an exo/endo ratio of about 70:30 to about 90:10 is achieved by reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.). In certain embodiments, an exo/endo ratio of about 80:20 to about 90:10 is achieved by reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.). In certain embodiments, an exo/endo ratio of approximately 75:25 is achieved by reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.). In certain embodiments, an exo/endo ratio of approximately 84:16 is achieved by reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.).

Compound (1) can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield. In certain embodiments, Compound (1) is isolated in greater than 50% yield. In certain embodiments, Compound (1) is isolated in about 50-60% yield. The compound may be isolated as a mixture or endo and exo products as described above and herein.

In certain embodiments, Compound (1) can be prepared and isolated in high chemical purity by a method described herein. In certain embodiments, the Compound (1) is isolated in greater than 50%, 55%, 60%, 65%, 70%, 75%, 80%, 85%, 90%, 95%, 98%, or 99% purity. In certain embodiments, Compound (1) is isolated in greater than 90% purity. In certain embodiments, Compound (1) is isolated in greater than 95% purity. In certain embodiments, Compound (1) is isolated in greater than 98% purity. In certain embodiments, Compound (1) is isolated in greater than 99% purity.

Any chemical yield can be achieved by, in certain embodiments, reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.). For example, in certain embodiments, a chemical yield for Compound (1) of at least 50% can be achieved by reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.). In certain embodiments, a chemical yield for Compound (1) of 50-60% can be achieved by reacting Compound (2) with furan in the absence of added acid, at approximately atmospheric pressure, in an aprotic polar solvent (e.g., NMP), with heating above room temperature (e.g., between room temperature and 100° C., e.g., between 40 and 50° C.).

After formation, Compound (1) may be purified via one or more purification steps. For example, in certain embodiments, Compound (1) is purified by chromatography, extraction, filtration, precipitation, crystallization, trituration, or any other method known in the art. In certain embodiments, the compound is carried forward to a subsequent synthetic step without purification (i.e., crude). In certain embodiments, the purification step improves the exo/endo ratio of the product mixture.

In certain embodiments, the reaction to prepare Compound (1) described herein is followed by a step of recrystallizing Compound (1). Compound (1) may be recrystallized from any solvent or mixture of solvents. In certain embodiments, Compound (1) is dissolved in a solvent, and then a second solvent is added to the solution to facilitate the precipitation of recrystallized Compound (1). For instance, in certain embodiments, Compound (I) is recrystallized from ethyl acetate (EtOAc) and hexanes. For example, Compound (1) may be dissolved in EtOAc, and crystalline Compound (1) precipitates upon addition of hexanes to the solution. The step of recrystallizing may involve heating and/or cooling the solution.

In certain embodiments, the step of recrystallization improves the exo/endo ratio of the compound mixture. In certain embodiments, Compound (1) is isolated in an exo/endo ratio of greater than 90:10 after recrystallization. For example, in certain embodiments, Compound (1) is isolated in an exo/endo ratio of 95:5, 96:4, 97:3, 98:2, or 99:1 after recrystallization. In certain embodiments, Compound (1) is isolated in greater than 30% yield after recrystallization. For example, in certain embodiments, Compound (1) is isolated in 30-40% yield after recrystallization.

As described herein, Compound (1) can be formed via a Diels-Alder reaction of Compound (2) with furan without the aid of acid or increased pressure. This invention is significant for several reasons. Based on the work of Dauben in the 1980s (See, e.g., *JACS,* 102, 6893(1980) and *JOC,* 50, 2576-2578 (1985)), this Diels-Alder cycloaddition was expected to require exotic, highly demanding reaction conditions, such as extreme pressures. At the time, precedent demonstrated that a retro Diels-Alder reaction of dehydrocantharidin and related systems was facile. Recognizing this, Dauben used exceedingly high pressures (>7 kbar) to force the cycloaddition of Compound (2) to Compound (1). Later on, Grieco (see, e.g., *JACS,* 112, 4595-459 (1990)) used highly concentrated ethereal solutions of lithium perchlorate (a Lewis acid) to promote the reaction. A second Grieco method using lithium trifluoromethanesulfonimide (a Lewis acid) also yielded the desired adduct (1), but with erosion of the favorable exo-endo ratio. As noted herein, neither the Dauben nor the Grieco conditions are viable large-scale production methods for a commercial product. It was later discovered that alternative Lewis acids could replace the lithium Lewis acids in the Grieco procedure (International Publication No. WO 2016/100732, published Jun. 23, 2016, the entire contents of which is incorporated herein by reference).

The discovery that Compound (1) can be formed using the reaction conditions described herein is a surprising advancement. In particular, it is unexpected that Compound (1) can be formed from Compound (2) in the absence of an acid promoter or with the aid of pressure. For example, in certain embodiments, mixing a solution of the two reactions in an aprotic polar solvent (e.g, acetonitrile, NMP, DMPU, and acetone) with modest warming yields Compound (1) with a favorable ratio of exo-endo isomers (e.g., greater than 80:20). Furthermore, in certain embodiments, isolation of the desired product Compound (1) could readily be accomplished in favorable yield and in high purity. The fact that such simple reaction conditions are all that is required for successful formation of adduct (1) from Compound (2) and furan is surprising and unexpected based on 37 years of precedent. The success of these specific Diels-Alder conditions was not predicted for these two substrates. Notably, these new reactions conditions are quite suitable for industrial-scale production of cantharidin. A reaction mixture consisting essentially of Compound (2), furan, and solvent is ideal for commercial production as industrial hazards and toxic waste disposal are minimized.

As described herein, Compound (1) can be used to prepare cantharidin, for example, as shown in Scheme 6. Compound (1) can be hydrogenated and reduced to form cantharidin. In certain embodiments, the steps of hydrogenation and reduction are carried out in the same reaction. In other embodiments, the steps of hydrogenation and reduction are carried out in separate, subsequent reactions.

Scheme 6

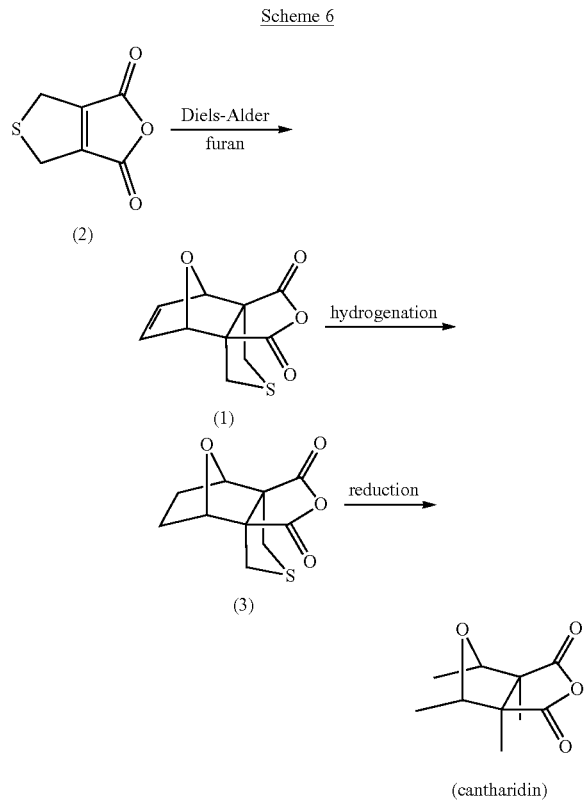

Therefore, in certain embodiments, a method provided herein further comprises a step of hydrogenating Compound (1):

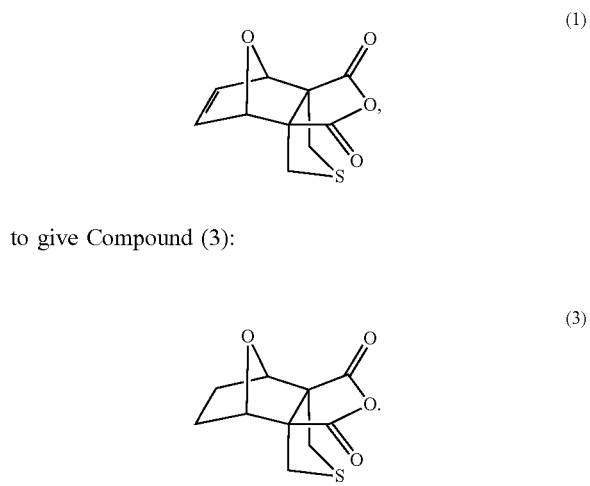

to give Compound (3):

The hydrogenation reaction may be carried out in the presence of palladium or platinum. The hydrogenation reaction may be performed using, for example, Pd/C, Pd, PdCl$_2$, PtO$_2$, or Pt/C. In certain embodiments, the reaction may be performed in the presence of H$_2$. The reaction may be carried out under transfer hydrogenation conditions (e.g., in the presence of 1,4-cyclohexadiene). The hydrogenation reaction may be carried out as described in international Publication No. WO 2016/100732, published Jun. 23, 2016, the entire contents of which is incorporated herein by reference.

The hydrogenation reaction may be performed in a solvent. Examples of solvents are provided herein. In certain embodiments, the solvent is ethyl acetate. The reaction can be carried out at any concentration of the reactants in solvent or reaction mixture. In certain embodiments, the concentration of Compound (1) in solvent or reaction mixture is approximately 0.01 molar (mol/L, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 120° C., 130° C., 140° C., or 150° C. In certain embodiments, the reaction temperature is greater than 150° C. in certain embodiments, the reaction temperature is approximately room temperature (21° C. or 70° F.). In certain embodiments, the reaction is carried out at a temperature above room temperature. In certain embodiments, the temperature is between room temperature and 100° C.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

Compound (3) can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

In certain embodiments, Compound (3) can be prepared and isolated in high chemical purity by a method described herein. In certain embodiments, Compound (3) is isolated in greater than 50%, 55%, 60%, 65%, 70%, 75%, 80%, 85%, 90%, 95%, 98%, or 99% purity. In certain embodiments, Compound (3) is isolated in greater than 90% purity. In certain embodiments, Compound (3) is isolated in greater than 95% purity. In certain embodiments, Compound (3) is isolated in greater than 98% purity. In certain embodiments, Compound (3) is isolated in greater than 99% purity.

After formation, Compound (3) may be purified via one or more purification steps. For example, in certain embodiments, Compound (3) is purified by chromatography, extraction, filtration, precipitation, crystallization, or any other method known in the art. In certain embodiments, the compound is carried forward to a subsequent synthetic step without purification (i.e., crude).

In certain embodiments, as shown in Scheme 6, the method further comprises a step of reducing Compound (3):

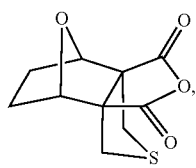

(3)

to yield cantharidin:

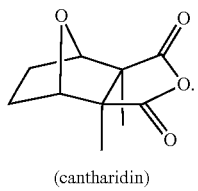

(cantharidin)

In certain embodiment, the reduction (also referred to as "desulfurization") is carried out in the presence of a reducing agent. In certain embodiments, the reducing agent is Raney Nickel, Ni(II)/NaBH$_4$, Co(II)/NaBH$_4$, Li/EtNH$_2$, LAH/TiCl$_3$, LAH/CuCl$_2$, Ni(II)/Zn, Ni(II)/Al, or LAH/Cp$_2$Ni. In certain embodiments, the reducing agent is Raney Ni.

The reduction may be performed in a solvent. Examples of solvents are provided herein. The reaction can be carried out at any concentration of the reactants in solvent or reaction mixture. In certain embodiments, the concentration of Compound (3) in solvent or reaction mixture is approximately 0.01 molar (mol/L, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2M, 3M, 4M, 5M, 6M, 7M, 8M, 9M, or 10M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 0.120° C., 130° C., 0.140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 0.100° C. Reaction temperatures can be from −20° C. to 100° C., in other embodiments. In some instances, these reactions can be facilitated with the aid of sonication or microwave heating.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

Cantharidin can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

After formation, cantharidin may be purified via one or more purification steps. For example, in certain embodiments, cantharidin is purified by chromatography, extraction, filtration, precipitation, crystallization, or any other method known in the art. In certain embodiments, the compound is carried forward to a subsequent synthetic step without purification (i.e., crude).

In certain embodiments, the steps of hydrogenating and reducing are carried out in separate reactions. In certain embodiments, the steps of hydrogenating and reducing are carried out in the same reaction. The steps of hydrogenating and reducing can be carried out in any order. Other examples of reagents and conditions useful in these hydrogenation and desulfurization reactions can be found in, e.g., International Publication No. WO 2016/100732, published Jun. 23, 2016, the entire contents of which is incorporated herein by reference.

In certain embodiments, cantharidin can be prepared and isolated in high chemical purity by a method described herein. In certain embodiments, cantharidin is isolated in greater than 50%, 55%, 60%, 65%, 70%, 75%, 80%, 85%, 90%, 95%, 98%, or 99% purity. In certain embodiments, cantharidin is isolated in greater than 90% purity. In certain embodiments, cantharidin is isolated in greater than 95% purity. In certain embodiments, cantharidin is isolated in greater than 98% purity. In certain embodiments, cantharidin is isolated in greater than 99% purity. In certain embodiments, cantharidin is isolated in greater than 99.1%. 99.2%, 99.3%, 99.4%, 99.5%, 99.6%, 99.7%, 99.8%, or 99.9% purity.

Also provided herein are high-purity cantharidin compositions produced by any method described herein. A high-purity cantharidin composition, as described herein, is high-purity with respect to the cantharidin component of the composition (i.e., not taking into account other active agents, excipients, carriers, solvents, etc. present in the composition). For instance, a high-purity cantharidin component of a composition comprises a high concentration of cantharidin with respect to synthetic intermediates, reaction byproducts, or degradation products of cantharidin. In certain embodiments, the purity is greater than 50%, 55%, 60%, 65%, 70%, 75%, 80%, 85%, 90%, 95%, 98%, or 99% with respect to the cantharidin component. In certain embodiments, the purity is greater than 90% with respect to the cantharidin component. In certain embodiments, the purity is greater than 95% with respect to the cantharidin component. In certain embodiments, the purity is greater than 98% with respect to the cantharidin component. In certain embodiments, the purity is greater than 99% with respect to the cantharidin component. In certain embodiments, the purity is greater than 99.1%. 99.2%, 99.3%, 99.4%, 99.5%, 99.6%, 99.7%, 99.8%, or, 99.9% purity.

Other Methods Useful in the Synthesis of Cantharidin

Scheme 5 outlines other methods provided herein which are useful in the preparation of cantharidin and analogs thereof. Specifically, intermediates of Formula (IV) can be formed via novel Diels-Alder reaction between compounds of Formula (III) and furan. The Diels-Alder reaction can proceed with or without the aid of acid (e.g., Lewis acid), and with or without the aid of increased pressure. In certain embodiments, the Diels-Alder reaction proceeds without the aid of added acid, and without the aid of increased pressure (i.e., at around atmospheric pressure). Compounds of Formula (IV) can then be hydrogenated to provide compounds of Formula (V). Compounds of Formula (V) can then be transformed to cantharidin via two alternative routes, as shown in Scheme 5.

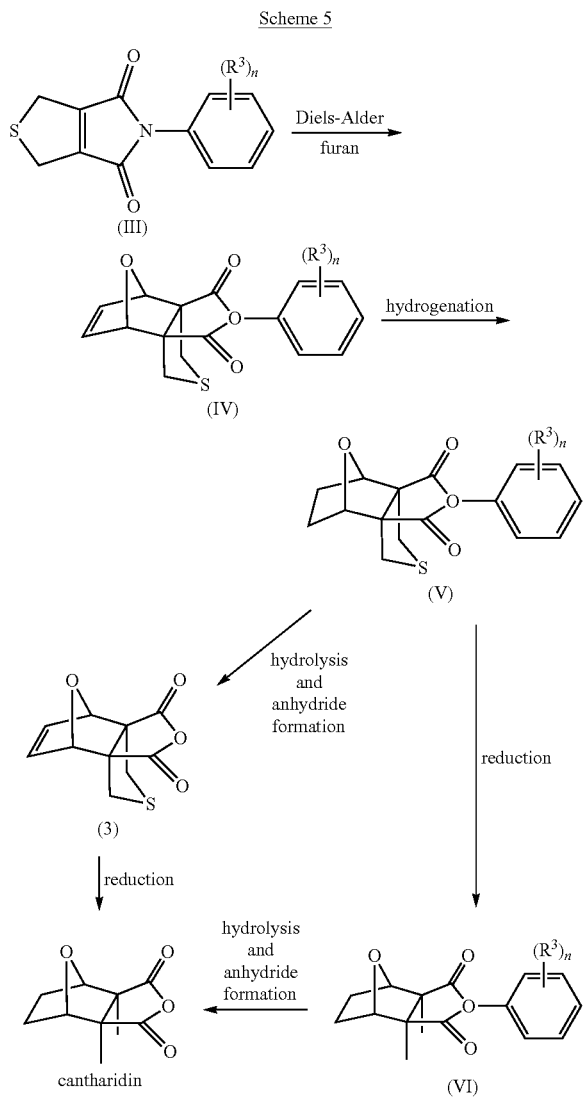

Provided herein are methods of preparing a compound of Formula (IV):

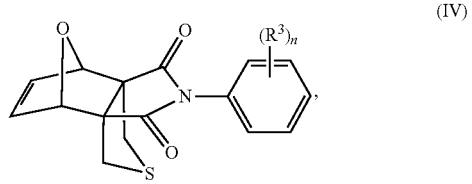

the methods comprising reacting a compound of Formula (III):

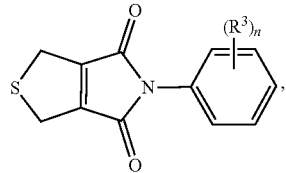

in the presence of furan, wherein:

n is 0, 1, 2, 3, 4, or 5;

each instance of $R^3$ is independently hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)$_2$, or —SR$^S$;

each instance of R$^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;

each instance of R$^N$ is independently hydrogen, optionally substituted alkyl, optionally substituted alkenyl, optionally substituted carbocyclyl, optionally substituted heterocyclyl, optionally substituted aryl, optionally substituted heteroaryl, optionally substituted acyl, or a nitrogen protecting group; or optionally two R$^N$ on the same nitrogen are joined together with the intervening atoms to form optionally substituted heterocyclyl or optionally substituted heteroaryl; and each instance of R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

In certain embodiments, the reaction is carried out in the presence of a Lewis acid. At least one Lewis acid may contain a Lewis metal selected from the group consisting of: Li(I), Mg(II), B(III), Al(III), Ti(IV), Zr(IV), Zn(II), Cu(I), Cu(II), Sn(II), Sn(IV), Si(IV), La(III), Sc(III), Yb(III), Eu(III), Ga(III), Sb(V), Nb(V), Fe(III), and Co(III). At least one Lewis acid may be selected from lithium perchlorate, magnesium perchlorate, aluminum chloride, lithium trifluoromethanesulfonate, lithium trifluoromethanesulfonamide, tin(II) trifluoromethanesulfonate, bis(cyclopentadienyl)zirconium(IV) bis(trifluoromethanesulfonate)tetrahydrofuran complex, bis(cyclopentadienyl)titanium(IV) bis(trifluoromethanesulfonate), boron trifluoride diethyl etherate, and gallium(III) chloride. At least one Lewis acid may be selected from copper(II) tetrafluoroborate hydrate, aluminum bromide, niobium(V) chloride, ytterbium(III) trifluoromethanesulfonate, scandium(III) trifluoromethanesulfonate, magnesium trifluoromethanesulfonate, trimethylsilyl trifluoromethanesulfonate, and copper(II) trifluoromethanesulfonate. The concentration of Lewis acid may be greater than or equal to 0.01 molar (moles/liter, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, or 10 M.

The reaction can be carried out at any pressure. In certain embodiments, the reaction is carried out at a pressure of less than or equal to about 1000 atmospheres (atm), 980 atm, 975 atm, 950 atm, 925 atm, 900 atm, 875 atm, 850 atm, 825 atm, 800 atm, 775 atm, 750 atm, 725 atm, 700 atm, 675 atm, 650 atm, 625 atm, 600 atm, 575 atm, 550 atm, 525 atm, 500 atm, 475 atm, 450 atm, 425 atm, 400 atm, 375 atm, 350 atm, 325 atm, 300 atm, 275 atm, 250 atm, 225 atm, 200 atm, 175 atm, 150 atm, 125 atm, 100 atm, 75 atm, 50 atm, 45 atm, 40 atm, 35 atm, 30 atm, 25 atm, 20 atm, 15 atm, 10 atm, 9 atm, 8 atm, 7 atm, 6 atm, 5 atm, 4 atm, 3 atm, 2 atm, or 1 atm. in certain embodiments, the reaction is carried out at a pressure above 1000 atmospheres (atm).

The Diels-Alder reaction described may be carried out in the absence of an acid. In certain embodiments, the reaction is carried out in the absence of added acid (i.e., no acid is added to the reaction mixture). In certain embodiments, the reaction is carried out in the absence of an added Lewis acid or Brønsted acid. In certain embodiments, the reaction mixture consists essentially of the compound of Formula (lii), furan, and solvent.

In certain embodiments, the reaction is carried out in the absence of a perchlorate. In certain embodiments, the reaction is carried out in the absence of magnesium perchlorate (Mg $ClO_4$). In certain embodiments, the reaction is carried out in the absence of lithium perchlorate ($LiClO_4$). In certain embodiments, the reaction is carried out in the absence of bis(trifluoromethanesulfonyl)imide. In certain embodiments, the reaction is carried out in the absence of one or more Lewis acids described in International Publication No. WO 2016/100732, published Jun. 23, 2016, the entire contents of which is incorporated herein by reference.

The Diels-Alder reaction provided above may be carried out in the absence of increased pressure (i.e., at approximately atmospheric pressure (1 atm)).

In certain embodiments, the reaction is carried out in a solvent. In certain embodiments, the solvent is a nonpolar or polar solvent. In certain embodiments, the solvent is a polar solvent. For instance, in certain embodiments, reaction may be performed in acetone, toluene, benzene, xylenes, chlorobenzene, methylene chloride, ethylene dichloride, dioxane, tetrahydrofuran (THF), tert-butyl methyl ether, diisopropyl ether, 1,2-dimethoxyethane (glyme), acetonitrile, ethyl acetate, isopropyl acetate, water, or a mixture thereof as the solvent.

In certain embodiments, the solvent is an amide, lactam, or urea such as N,N-dimethylformamide (DMF), N-methyl-2-pyrrolidone (NMP), 1,3-dimethyl-2-imidazolidinone (DMI), or 1,3-dimethyl-3,4,5,6-tetrahydro-2(1H)-pyrimidinone (DMPU). In certain embodiments, the solvent is a sulfone solvent such as dimethyl sulfone, dimethyl sulfoxide (DMSO), or sulfolane. In certain embodiments, the solvent is NMP. In certain embodiments, the solvent is a co-solvent comprising NMP. Other examples of polar solvents include, but are not limited to, ketones and nitriles, such as acetone and acetonitrile. In certain embodiments, an aprotic polar solvent is selected from the group consisting of DMF, NMP, DM1, DMPU, acetone, and acetonitrile. In certain embodiments, an aprotic polar solvent is selected from the group consisting of NMP, DMPU, acetone, and acetonitrile.

In certain embodiments, the reaction is carried out in the absence of solvent. In certain embodiments, the reaction is carried out in an ionic liquid. In certain embodiments, the reaction is carried out in a ball-mill reactor.

The reaction can be carried out at any concentration of the reactants in solvent or reaction mixture. In certain embodiments, the concentration of the compound of. Formula (III). In solvent or reaction mixture is approximately 0.01 molar (mol L, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, or 10 M. In certain embodiments, the reaction is carried out at a concentration of 1-20 M in solution with respect to the compound of Formula (111). In certain embodiments, the concentration is 5-15 M. In certain embodiments, the concentration is 10-15 M.

The reaction may be carried out at any temperature. The reaction temperature may be approximately –100° C., –90° C., –80° C., –78° C., –70° C., –60° C., –50° C., –40° C., –30° C., –20° C., –10, 0° C., –10° C., 20° C., room temperature, 30° C., 40° C., 50° C., 60° C., 70° C., 80° C., 90° C., 100° C., 110° C., 1.20° C., 130° C., 140° C., or 150° C. In certain embodiments, the reaction temperature is above 100° C. in certain embodiments, the reaction is carried out at a temperature below 100° C. In certain embodiments, the reaction is carried out at a temperature above room temperature (21° C. or 70° F.). In certain embodiments, the temperature is between room temperature and 100° C. In certain embodiments, the reaction is carried out at a temperature between 30 and 60° C. In certain embodiments, the reaction is carried out at a temperature between 40 and 50° C. In certain embodiments, the reaction is carried out at approximately 40° C. 41° C., 42° C., 43° C., 44° C., 45° C., 46° C., 47° C., 48° C., 49° C., or 50° C. In certain embodiments, the reaction is carried out at around 45° C.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

The reaction mixture may contain any ratio of the reactants, specifically, the compound of Formula (III) and furan. In certain embodiments, furan is present in greater than 1 equivalent relative to the amount of the compound of Formula (III) in the reaction mixture (i.e., excess). In certain embodiments, the ratio of the compound of Formula (III) to furan in the reaction mixture is from 1:1 to 1:20. In certain embodiments, the ratio of the compound of Formula (III) and furan in the reaction mixture is from 1:1 to 1:10. In certain embodiments, the ratio of the compound of Formula (III) to furan in the reaction mixture is approximately 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the ratio of the compound of Formula (III) to furan in the reaction mixture is from 1:4 to 1:5. In certain embodiments, the ratio of the compound of Formula (III) to furan in the reaction mixture is about 1:4.1, 1:4.2, 1:4.3, 1:4.4, 1:4.5, 1:4.6, 1:4.7, 1:4.8, or 1:4.9.

As described herein, the reaction may be carried out in the absence of added acid at approximately 1 atm. In some instances, the reaction solvent and temperature may be varied as follows. In certain embodiments, the reaction is carried out in a polar solvent at room temperature or above. In certain embodiments, the reaction is carried out in a polar solvent between room temperature and 100° C. in certain embodiments, the reaction is carried out in a polar solvent at elevated temperature (i.e., above room temperature). In certain embodiments, the reaction is carried out in a polar solvent at a temperature between room temperature and 100° C. In certain embodiments, the reaction is carried out in a polar solvent at a temperature between 30° C. and 100° C. In certain embodiments, the reaction is carried out in a polar solvent at a temperature between 30° C. and 60° C. In certain embodiments, the reaction is carried out in a polar solvent at a temperature between 40° C. and 50° C. In certain embodiments, the reaction is carried out in a polar solvent at a temperature around 50° C. In certain embodiments, the reaction is carried out in an aprotic polar solvent at a temperature around 45° C. In certain embodiments, the reaction is carried out in a polar solvent at a temperature around 40° C. in certain embodiments, the reaction is carried out in NMP at room temperature or above. In certain embodiments, the reaction is carried out in NMP at between room temperature and 100° C. in certain embodiments, the reaction is carried out in NMP at elevated temperature (i.e., above room temperature). In certain embodiments, the reaction is carried out in NMP at a temperature between room temperature and 100° C. In certain embodiments, the reaction is carried out in NMP at a temperature between 30° C. and 100° C. In certain embodiments, the reaction is carried out in NMP at a temperature between 30° C. and 60° C. In certain embodiments, the reaction is carried out in NMP at a temperature between 40° C. and 50° C. In certain embodiments, the reaction is carried out in NMP at a temperature around 50° C. In certain embodiments, the reaction is carried out in NMP at a temperature around 45° C. In certain embodiments, the reaction is carried out in NMP at a temperature around 40° C.

In the methods provided herein, the compound of Formula (IV) can be formed as the exo or endo cycloadduct, or as a mixture of exo and endo cycloadducts. The "exo" and "endo" adducts are shown below:

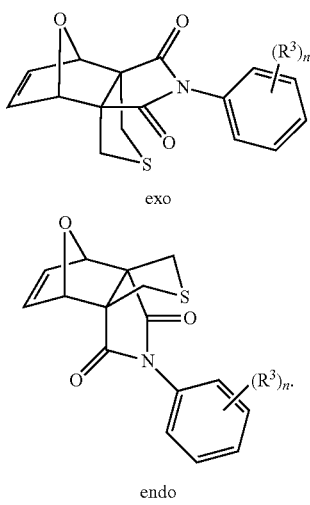

For cantharidin, a high exo-to-endo ratio is desired. In certain embodiments, the Diels-Alder methods provided herein yield a favorable exo-to-endo ratio. For instance, the exo-to-endo product ratios produced by methods disclosed herein can be at least about 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or 100:0. The percentage of exo product per total amount of product can be at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 99.99%, 99.999%, or 100%. In certain embodiments, the exo/endo ratio is from about 70:30 to 99:1. In certain embodiments, the exo/endo ratio is from about 70:30 to 90:10. In certain embodiments, the exo/endo ratio is from about 70:30 to 80:20. In certain embodiments, the exo/endo ratio is about 70:30, 71:29, 72:28, 73:27, 74:26, 75:25, 76:24, 77:23, 78:22, 79:21, or 80:20. In certain embodiments, the exo/endo ratio is about 75:25. In certain embodiments, the exo/endo ratio is from about 80:20 to about 90:10. In certain embodiments, the exo/endo ratio is about 80:20. In certain embodiments, the exo/endo ratio is about 81:19. In certain embodiments, the exo/endo ratio is about 82:18. In certain embodiments, the exo/endo ratio is about 83:17. In certain embodiments, the exo/endo ratio is about 84:16. In certain embodiments, the exo/endo ratio is about 85:15. In certain embodiments, the exo/endo ratio is about 86:14. In certain embodiments, the exo/endo ratio is about 87:13. In certain embodiments, the exo/endo ratio is about 88:12. In certain embodiments, the exo/endo ratio is about 89:11. In certain embodiments, the exo/endo ratio is about 90:10. In certain embodiments, the exo/endo ratio is about 95:5. In certain embodiments, the exo/endo ratio is about 98:2. In certain embodiments, the exo/endo ratio is about 99:1. In certain embodiments, the exo/endo ratio is about 99.10:0.10.

The compound of Formula (IV) can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield. In certain embodiments, the compound of Formula (IV) is isolated in greater than 50% yield.

In certain embodiments, the compound of Formula (IV) can be prepared and isolated in high chemical purity by a method described herein. In certain embodiments, the compound of Formula (IV) is isolated in greater than 50%, 55%, 60%, 65%, 70%, 75%, 80%, 85%, 90%, 95%, 98%, or 99% purity. In certain embodiments, the compound of Formula (IV) is isolated in greater than 90% purity. In certain embodiments, the compound of Formula (IV) is isolated in greater than 95% purity. In certain embodiments, the compound of Formula (IV) is isolated in greater than 98% purity. In certain embodiments, the compound of Formula (IV) is isolated in greater than 99% purity.

After formation, the compound of Formula (IV) may be purified via one or more purification steps. For example, in certain embodiments, the compound of Formula (IV) is purified by chromatography, extraction, filtration, precipitation, crystallization, trituration, or any other method known in the art. In certain embodiments, the compound is carried forward to a subsequent synthetic step without purification (i.e., crude). In certain embodiments, the purification step improves the exo/endo ratio of the product mixture.

In certain embodiments, the reaction to prepare the compound of Formula (IV) described herein is followed by a step of recrystallizing the compound of Formula (IV). The compound of Formula (IV) may be recrystallized from any solvent or mixture of solvents. In certain embodiments, the compound of Formula (IV) is dissolved in a solvent, and then a second solvent is added to the solution to facilitate the precipitation of recrystallized the compound of Formula (IV).

In certain embodiments, the step of recrystallization improves the exo/endo ratio of the compound mixture. In certain embodiments, the compound of Formula (IV) is isolated in an exo/endo ratio of greater than 90:10 after recrystallization. For example, in certain embodiments, the compound of Formula (IV) is isolated in an exo/endo ratio of 95:5, 96:4, 97:3, 98:2, or 99:1 after recrystallization.

Also provided herein are methods of preparing a compound of Formula (V):

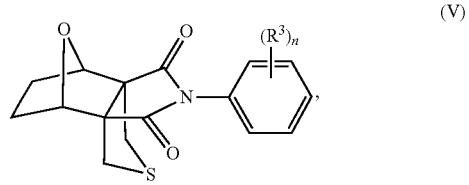

the methods comprising hydrogenating a compound of Formula (IV):

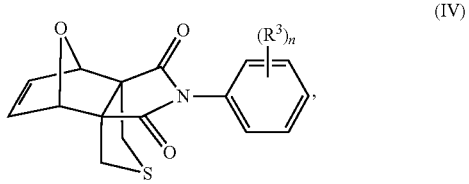

wherein:
  n is 0, 1, 2, 3, 4, or 5;
  each instance of $R^3$ is independently hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)$_2$, or —SR$^S$;
  each instance of R$^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
  each instance of R$^N$ is independently hydrogen, optionally substituted alkyl, optionally substituted alkenyl, optionally substituted carbocyclyl, optionally substituted heterocyclyl, optionally substituted aryl, optionally substituted heteroaryl, optionally substituted acyl, or a nitrogen protecting group; or optionally two R$^N$ on the same nitrogen are joined together with the intervening atoms to form optionally substituted heterocyclyl or optionally substituted heteroaryl;
  each instance of R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

The hydrogenation may be carried out in the presence of palladium or platinum. The hydrogenation reaction may be performed using, for example, Pd/C, Pd, PdCl$_2$, PtO$_2$, or Pt/C. In certain embodiments, the reaction may be performed in the presence of H$_2$. The reaction may be carried out under transfer hydrogenation conditions (e.g., in the presence of 1,4-cyclohexadiene). Other reagents/conditions useful in the hydrogenation reaction are described in, e.g., International Publication No. WO 2016/100732, published Jun. 23, 2016, the entire contents of which is incorporated herein by reference.

The hydrogenation reaction may be performed in a solvent. Examples of solvents are provided herein. In certain embodiments, the solvent is ethyl acetate. The reaction can be carried out at any concentration of the reactants in solvent or reaction mixture. In certain embodiments, the concentration of the compound of Formula (IV) in solvent or reaction mixture is approximately 0.01 molar (mol/L, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8 M, 9 M, or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 120° C., 130° C., 140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 100° C.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

The compound of Formula (V) can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

In certain embodiments, the compound of Formula (V) can be prepared and isolated in high chemical purity by a method described herein. In certain embodiments, the compound is isolated in greater than 50%, 55%, 60%, 65%, 70%, 75%, 80%, 85%, 90%, 95%, 98%, or 99% purity. In certain embodiments, the compound of Formula (V) is isolated in greater than 90% purity. In certain embodiments, the compound of Formula (V) is isolated in greater than 95% purity. In certain embodiments, the compound of Formula (V) is isolated in greater than 98% purity. In certain embodiments, the compound of Formula (V) is isolated in greater than 99% purity.

After formation, the compound of Formula (V) may be purified via one or more purification steps. For example, in certain embodiments, the compound of Formula (V) is purified by chromatography, extraction, filtration, precipitation, crystallization, or any other method known in the art. In certain embodiments, the compound is carried forward to a subsequent synthetic step without purification (i.e., crude).

Also provided herein is a method of preparing a compound of Formula (VI):

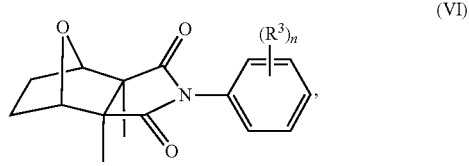

(VI)

the method comprising reducing a compound of Formula (V):

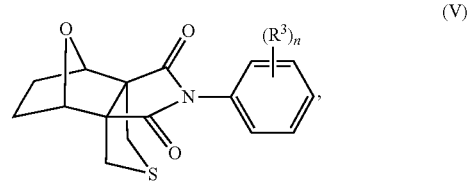

(V)

wherein:
n is 0, 1, 2, 3, 4, or 5;
each instance of $R^3$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —$OR^O$, —$N(R^N)_2$, or —$SR^S$;
each instance of $R^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
each instance of $R^N$ is independently hydrogen, optionally substituted alkyl, optionally substituted alkenyl, optionally substituted alkenyl, optionally substituted carbocyclyl, optionally substituted heterocyclyl, optionally substituted aryl, optionally substituted heteroaryl, optionally substituted acyl, or a nitrogen protecting group; or optionally two $R^N$ on the same nitrogen are joined together with the intervening atoms to form optionally substituted heterocyclyl or optionally substituted heteroaryl; and
each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

In certain embodiment, the reduction (also referred to as "desulfurization") is carried out in the presence of a reducing agent. In certain embodiments, the reducing agent is Raney Nickel, Ni(II)/$NaBH_4$, Co(II)/$NaBH_4$, Li/$EtNH_2$, LAH/$TiCl_3$, LAH/$CuCl_2$, Ni(II)/Zn, Ni(II)/Al, or LAH/$Cp_2Ni$. In certain embodiments, the reducing agent is Raney Ni. Other reagents/conditions useful in the reduction reaction are described in, e.g., International Publication No. WO 2016/100732, published Jun. 23, 2016, the entire contents of which is incorporated herein by reference.

The reduction may be performed in a solvent. Examples of solvents are provided herein. The typical solvents for desulfurization reactions can be alcohols, ethers, ester-based solvents and water or various mixtures of these solvents. The reaction can be carried out at any concentration of the reactants in solvent or reaction mixture. In certain embodiments, the concentration of the compound of Formula (V) in solvent or reaction mixture is approximately 0.01 molar (mol/L, M), 0.02 M, 0.03 M, 0.04 M, 0.05 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4M, 5M, 6M, 7M, 8M, 9M, or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 120° C., 0.130° C., 140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 100° C. Reaction temperatures can be from −20° C. to 100° C., in other embodiments. In some instances, these reactions can be facilitated with the aid of sonication or microwave heating.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

The compound of Formula (V1) can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

In certain embodiments, the compound of Formula (VI) can be prepared and isolated in high chemical purity by a method described herein. In certain embodiments, the compound of Formula (VI) is isolated in greater than 50%, 55%, 60%, 65%, 70%, 75%, 80%, 85%, 90%, 95%, 98%, or 99% purity. In certain embodiments, the compound of Formula (VI) is isolated in greater than 90% purity. In certain embodiments, the compound of Formula (VI) is isolated in greater than 95% purity. In certain embodiments, the compound of Formula (VI) is isolated in greater than 98% purity. In certain embodiments, the compound of Formula (VI) is isolated in greater than 99% purity.

After formation, the compound of Formula (VI) may be purified via one or more purification steps. For example, in certain embodiments, the compound of Formula (VI) is purified by chromatography, extraction, filtration, precipitation, crystallization, or any other method known in the art. In certain embodiments, the compound is carried forward to a subsequent synthetic step without purification (i.e., crude).

Also provided herein is a method of preparing cantharidin:

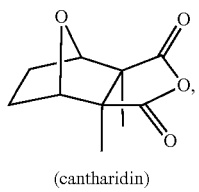

(cantharidin)

the method comprising:
(a) hydrolyzing a compound of Formula (VI):

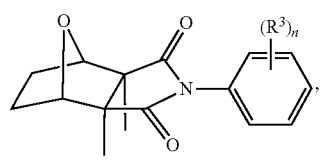

to yield a compound of the formula:

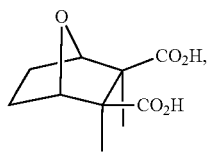 [SMILES: CC1(C(=O)O)C2CCCC(O2)C1(C)C(=O)O]

or a salt thereof; and
(b) dehydrating the compound formed in step (a) under suitable conditions to form cantharidin; wherein:
n is 0, 1, 2, 3, 4, or 5;
each instance of $R^3$ is independently hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)$_2$, or —SR$^S$;
each instance of R$^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
each instance of R$^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two R$^N$ on the same nitrogen are joined together with the intervening atoms to form optionally substituted heterocyclyl or optionally substituted heteroaryl; and
each instance of R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

In certain embodiments, the step of hydrolyzing (i.e., step (a)) is carried out in the presence of a base. In certain embodiments, the base is a hydroxide (e.g., NaOH, KOH, LiOH). In certain embodiments, the hydrolysis is carried out in the presence of water.

The reduction may be performed in a solvent. The reaction can be carried out at any concentration of the reactants in solvent or reaction mixture. In certain embodiments, the concentration of the compound of Formula (VI) in solvent or reaction mixture is approximately 0.01 molar (mol/L, M), 0.02 M, 0.03 M, 0.04 M, 0.0.5 M, 0.06 M, 0.07 M, 0.08 M, 0.09 M, 0.1 M, 0.2M, 0.3M, 0.4M, 0.5M, 0.6M, 0.7M, 0.8M, 0.9M, 1 M, 2 M, 3 M, 4M, 5M, 6M, 7M, 8M, 9M, or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 0.120° C., 130° C., 0.140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 0.100° C. Reaction temperatures can be from −20° C. to 100° C., in other embodiments. In some instances, these reactions can be facilitated with the aid of sonication or microwave heating.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

The compound of the formula:

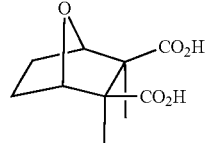 [SMILES: CC1(C(=O)O)C2CCCC(O2)C1(C)C(=O)O]

can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

In certain embodiments, the compound can be prepared and isolated in high chemical purity by a method described herein. In certain embodiments, the compound is isolated in greater than 50%, 55%, 60%, 65%, 70%, 75%, 80%, 85%, 90%, 95%, 98%, or 99% purity. In certain embodiments, the compound is isolated in greater than 90% purity. In certain embodiments, the compound is isolated in greater than 95% purity. In certain embodiments, the compound is isolated in greater than 98% purity. In certain embodiments, the compound is isolated in greater than 99% purity.

After formation, the compound of the formula:

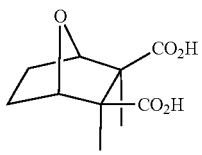 [SMILES: CC1(C(=O)O)C2CCCC(O2)C1(C)C(=O)O]

may be purified via one or more purification steps. For example, in certain embodiments, the compound of is purified by chromatography, extraction, filtration, precipitation, crystallization, or any other method known in the art. In certain embodiments, the compound is carried forward to a subsequent synthetic step without purification (i.e., crude).

In certain embodiments, the step of dehydrating (i.e., step (b)) is carried out in the presence of a reagent capable of effecting the dehydration. For example, in certain embodiments, acid chlorides, acid anhydrides, and mixed anhydrides (e.g., mixed anhydrides of sulfonic and phosphonic acids) can be used. In certain embodiments, propylphosphonic anhydride can be used. In certain embodiments, acetic anhydride, thionyl chloride, or $POCl_3$ can be used.

The reduction may be performed in a solvent. The reaction can be carried out at any concentration of the reactants in solvent or reaction mixture. In certain embodiments, the concentration of the starting material in solvent or reaction mixture is approximately 0.01 molar (mol/L, M), 0.02 M, 0.03M, 0.04M, 0.05M, 0.06M, 0.07M, 0.08M, 0.09M, 0.1 M, 0.2 M, 0.3 M, 0.4 M, 0.5 M, 0.6 M, 0.7 M, 0.8 M, 0.9 M, 1 M, 2 M, 3 M, 4 M, 5 M, 6 M, 7 M, 8M, 9M, or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 1.20° C., 130° C., 140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 100° C. Reaction temperatures can be from −20° C. to 100° C., in other embodiments. In some instances, these reactions can be facilitated with the aid of sonication or microwave heating.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

Cantharidin can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 5.5%, 60%, 65%, 70%, 75%, 80%, 85%, 90%, 95%, 98%, 99%, or 100% yield.

After formation, cantharidin may be purified via one or more purification steps. For example, in certain embodiments, cantharidin is purified by chromatography, extraction, filtration, precipitation, crystallization, or any other method known in the art. In certain embodiments, the compound is carried forward to a subsequent synthetic step without purification (i.e., crude).

In certain embodiments, cantharidin can be prepared and isolated in high chemical purity by a method described herein. In certain embodiments, cantharidin is isolated in greater than 50%, 55%, 60%, 65%, 70%, 75%, 80%, 85%, 90%, 95%, 98%, or 99% purity. In certain embodiments, cantharidin is isolated in greater than 90% purity. In certain embodiments, cantharidin is isolated in greater than 95% purity. In certain embodiments, cantharidin is isolated in greater than 98% purity. In certain embodiments, cantharidin is isolated in greater than 99% purity. In certain embodiments, cantharidin is isolated in greater than 99.1%. 99.2%, 99.3%, 99.4%, 99.5%, 99.6%, 99.7%, 99.8%, or 99.9% purity. Also provided herein is a high-purity cantharidin composition produced by any method described herein.

As shown in Scheme 5, also provided herein is a method of preparing a Compound (3):

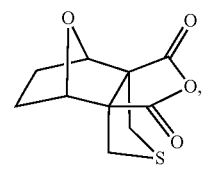

(3)

the method comprising steps of:
(a) hydrolyzing a compound of Formula (V):

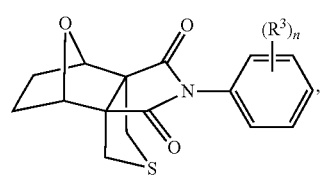

(V)

to yield a compound of the formula:

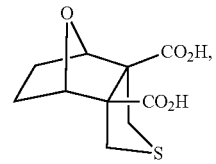 [SMILES: O=C(O)C12CSCC1(C(=O)O)C1CCCC2O1]

or a salt thereof; and
(b) dehydrating the compound formed in step (a) under suitable conditions to form Compound (3); wherein:
n is 0, 1, 2, 3, 4, or 5;
each instance of $R^3$ is independently hydrogen, halogen, —CN, —$NO_2$, —$N_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —$OR^O$, —$N(R^N)_2$, or —$SR^S$;

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ on the same nitrogen are joined together with the intervening atoms to form optionally substituted heterocyclyl or optionally substituted heteroaryl; and each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

In certain embodiments, the step of hydrolyzing (i.e., step (a)) is carried out in the presence of a base. In certain embodiments, the base is a hydroxide (e.g., NaOH, KOH, LiOH). In certain embodiments, the hydrolysis is carried out in the presence of water.

The reduction may be performed in a solvent. The reaction can be carried out at any concentration of the reactants in solvent or reaction mixture. In certain embodiments, the concentration of the compound of Formula (V) in solvent or reaction mixture is approximately 0.01 molar (mol/L, M), 0.02 M, 0.03 M, 0.04 M, 0.0.5 M, 0.06 M, 0.07 M, 0.08 M, 0.09 M, 0.1 M, 0.2 M, 0.3 M, 0.4 M, 0.5 M, 0.6 M, 0.7 M, 0.8 M, 0.9 M, 1 M, 2 M, 3 M, 4M, 5M, 6M, 7M, 8M, 9M or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 0.120° C., 130° C., 0.140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 0.100° C. Reaction temperatures can be from −20° C. to 100° C., in other embodiments. In some instances, these reactions can be facilitated with the aid of sonication or microwave heating.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

The compound of the formula:

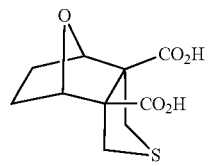 [SMILES: O=C(O)C12CSCC1(C(=O)O)C1CCCC2O1]

can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

In certain embodiments, the compound can be prepared and isolated in high chemical purity by a method described herein. In certain embodiments, the compound is isolated in greater than 50%, 55%, 60%, 65%, 70%, 75%, 80%, 85%, 90%, 95%, 98%, or 99% purity. In certain embodiments, the compound is isolated in greater than 90% purity. In certain embodiments, the compound is isolated in greater than 95% purity. In certain embodiments, the compound is isolated in greater than 98% purity. In certain embodiments, the compound is isolated in greater than 99% purity.

After formation, the compound of the formula:

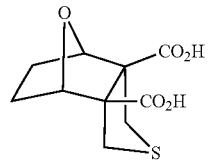 [SMILES: O=C(O)C12CSCC1(C(=O)O)C1CCCC2O1]

may be purified via one or more purification steps. For example, in certain embodiments, the compound of is purified by chromatography, extraction, filtration, precipitation, crystallization, or any other method known in the art. In certain embodiments, the compound is carried forward to a subsequent synthetic step without purification (i.e., crude).

In certain embodiments, the step of dehydrating (i.e., step (b)) is carried out in the presence of a reagent capable of effecting the dehydration. For example, in certain embodiments, acid chlorides, acid anhydrides, and mixed anhydrides (e.g., mixed anhydrides of sulfonic and phosphonic acids) can be used. In certain embodiments, propylphosphonic anhydride can be used. In certain embodiments, acetic anhydride, thionyl chloride, or POCl$_3$ can be used.

The reduction may be performed in a solvent. The reaction can be carried out at any concentration of the reactants in solvent or reaction mixture. In certain embodiments, the concentration of the starting material in solvent or reaction mixture is approximately 0.01 molar (mol/L, M), 0.02 M, 0.03 M, 0.04 M, 0.05 M, 0.06 M, 0.07 M, 0.08 M, 0.09 M, 0.1 M, 0.2M, 0.3M, 0.4M, 0.5M, 0.6M, 0.7M, 0.8M, 0.9M, 1 M, 2M, 3M, 4M, 5M, 6M, 7 M, 8 M, 9 M. or 10 M.

The reaction may be carried out at any temperature. The reaction temperature may be approximately −100° C., −90° C., −80° C., −78° C., −70° C., −60° C., −50° C., −40° C., −30° C., −20° C., −10, 0° C., −10° C., 20° C., room temperature, 30° C., 40° C., 50° C., 60° C., 70° C., 80° C., 90° C., 100° C., 110° C., 0.120° C., 130° C., 0.140° C., or 150° C. In certain embodiments, the reaction temperature is greater than 150° C. In certain embodiments, the reaction temperature is approximately room temperature (21° C. or 70° F.). In certain embodiments, the reaction is carried out at a temperature above room temperature. In certain embodiments, the temperature is between room temperature and 0.100° C. Reaction temperatures can be from −20° C. to 100° C., in other embodiments. In some instances, these reactions can be facilitated with the aid of sonication or microwave heating.

The reaction may be carried out over any length of time. The reaction time may be greater than or equal to 30 seconds, 1 minute, 5 minutes, 10 minutes, 30 minutes, 1 hour, 2 hours, 3 hours, 4 hours, 5 hours, greater than 5 hours, 10 hours, greater than 10 hours, 15 hours, or 20 hours. In certain embodiments, the reaction time is greater than 20 hours. In certain embodiments, the reaction time is greater than or equal to 1 day. In certain embodiments, the reaction time is greater than 1 day.

Compound (3) can be formed in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the compound is produced in approximately 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% yield.

In certain embodiments, Compound (3) can be prepared and isolated in high chemical purity by a method described herein. In certain embodiments, Compound (3) is isolated in greater than 50%, 55%, 60%, 65%, 70%, 75%, 80%, 85%, 90%, 95%, 98%, or 99% purity. In certain embodiments, Compound (3) is isolated in greater than 90% purity. In certain embodiments, Compound (3) is isolated in greater than 95% purity. In certain embodiments, Compound (3) is isolated in greater than 98% purity. In certain embodiments, Compound (3) is isolated in greater than 99% purity.

After formation, Compound (3) may be purified via one or more purification steps. For example, in certain embodiments, cantharidin is purified by chromatography, extraction, filtration, precipitation, crystallization, or any other method known in the art. In certain embodiments, the compound is carried forward to a subsequent synthetic step without purification (i.e., crude).

In certain embodiments, the method further comprises a step of reducing (i.e., desulfurizing) Compound (3) to yield cantharidin. This step can be carried out as described above and herein.

As defined herein, n is 0, 1, 2, 3, 4, or 5. In certain embodiments, n is 0. In certain embodiments, n is 1. In certain embodiments, n is 2. In certain embodiments, n is 3. In certain embodiments, n is 4. In certain embodiments, n is 5.

As defined herein, each instance of $R^3$ is independently hydrogen, halogen, —CN, —NO$_2$, —N$_3$, optionally substituted alkyl, optionally substituted alkenyl, optionally substituted alkenyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)$_2$, or —SR$^S$. In certain embodiments, at least one instance of $R^3$ is hydrogen. In certain embodiments, at least one instance of $R^3$ is halogen. In certain embodiments, at least one instance of $R^3$ is —CN. In certain embodiments, at least one instance of $R^3$ is —NO$_2$. In certain embodiments, at least one instance of $R^3$ is —N$_3$. In certain embodiments, at least one instance of $R^3$ is optionally substituted alkyl. In certain embodiments, at least one instance of $R^3$ is optionally substituted alkenyl. In certain embodiments, at least one instance of $R^3$ is optionally substituted alkynyl. In certain embodiments, at least one instance of $R^3$ is optionally substituted carbocyclyl. In certain embodiments, at least one instance of $R^3$ is optionally substituted heterocyclyl. In certain embodiments, at least one instance of $R^3$ is optionally substituted aryl. In certain embodiments, at least one instance of $R^3$ is optionally substituted heteroaryl. In certain embodiments, at least one instance of $R^3$ is optionally substituted acyl. In certain embodiments, at least one instance of $R^3$ is optionally substituted sulfonyl. In certain embodiments, at least one instance of $R^3$ is optionally substituted sulfinyl. In certain embodiments, at least one instance of $R^3$ is —OR$^O$. In certain embodiments, at least one instance of $R^3$ is —N(R$^N$)$_2$. In certain embodiments, at least one instance of $R^3$ is —SR$^S$.

Methods of Preparing Other Cantharidin Intermediates

Also provided herein are methods of preparing a compound of Formula (I), which is useful as an intermediate in the synthesis of cantharidin and analogs thereof. The methods of preparing a compound of Formula (I) involve a palladium-mediated carbonylation of a compound of Formula (II), as shown in Scheme 2 below.

Scheme 2

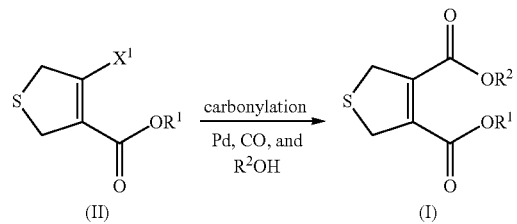

Provided herein are methods of preparing a compound of Formula (I):

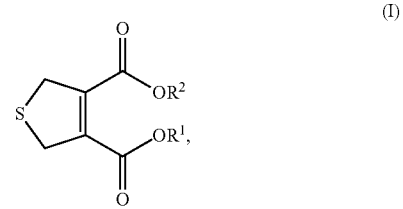

the method comprising reacting a compound of Formula (II):

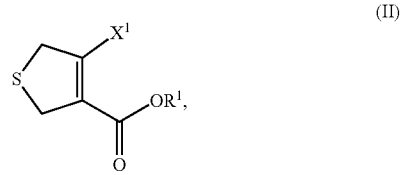

in the presence of palladium, carbon monoxide, and a reagent of the formula R$^2$OH; wherein:

$X^1$ is halogen, optionally substituted sulfonate, or optionally substituted phosphate;

$R^1$ and $R^2$ are independently optionally substituted alkyl, optionally substituted aryl, optionally substituted heteroaryl, optionally substituted carbocyclyl, optionally substituted heterocyclyl, or an oxygen protecting group.

The carbonylation reaction is carried out in the presence of palladium. In certain embodiments, the palladium is a palladium salt. In certain embodiments, the palladium, is a palladium(II) salt. Examples of palladium(II) salts include, but are not limited to, palladium chloride ($PdCl_2$), palladium acetate ($Pd(OAc)_2$), and palladium trifluoroacetate (Pd $(TFA)_2$). In certain embodiments, $Pd(OAc)_2$ is used. In certain embodiments, $Pd(PPh_3)_4$ is used. In certain embodiments, $Pd_2(dba)_3$ is used. In certain embodiments, one or more ligands are used in addition to the palladium source. For instance, in certain embodiments, $Pd_2(dba)_3$/dppf is used in the reaction. In other embodiments, $Pd(OAc)_2/PPh_3$ is used in the reaction.

The palladium source may be present in the reaction in a catalytic amount relative to the compound of Formula (II). For example, in certain embodiments, the palladium is present in approximately 1, 2, 3, 4, 5, 6, 7, 8.9, 10, 11, 12, 13, 14, 1.5, 1.6, 17, 18, 19, 20, 25, 30, 35, 40, 45, 50, 55, 60, 65, 70, 75, 80, 85, 90, 95, 98, or 99 mol % relative to the compound of Formula (II). In certain embodiments, the palladium is present in 1-10 mol %. In certain embodiments, the palladium is present in approximately 4 mol %. In certain embodiments, the palladium is present in approximately 5 mol %. In certain embodiments, the palladium is present in approximately 6 mol %.

The carbonylation reaction may be carried out in the presence of one or more palladium ligands. In certain embodiments, the reaction is carried out in the presence of a phosphine ligand. In certain embodiments, the reaction is carried out in the presence of a triarylphosphine ($(aryl)_3P$). In certain embodiments, the reaction is carried out in the presence of triphenylphosphine ($Ph_3P$). In certain embodiments, the reaction is carried out in the presence of 1,1'-bis (diphenylphosphino)ferrocene (dppf).

In certain embodiments, the phosphine is present in a catalytic amount. For example, in certain embodiments, the phosphine is present in approximately 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 98, or 99 mol % relative to the compound of Formula (II). In certain embodiments, the phosphine is present in approximately 1-10 mol %. In certain embodiments, the phosphine is present in approximately 1-20 mol %. In certain embodiments, the phosphine is present in approximately 10-20 mol %. In certain embodiments, the phosphine is present in approximately 3 mol %. In certain embodiments, the phosphine is present in approximately 14 mol %.

The carbonylation reaction is carried out in the presence of an alcohol of formula $R^2OH$. In certain embodiments, the alcohol is present in excess (i.e., greater than 1 equivalent with respect to the compound of Formula (II)). In certain embodiments, the alcohol of formula $R^2OH$ is present as a solvent or co-solvent. In certain embodiments, the alcohol is selected from the group consisting of methanol, ethanol, n-propanol, iso-propanol, n-butanol, iso-butanol, sec-butanol, and tert-butanol. In certain embodiments, the alcohol is methanol. In certain embodiments, the alcohol is ethanol. In certain embodiments, the alcohol is n-propanol. In certain embodiments, the alcohol is iso-propanol. In certain embodiments, the alcohol is n-butanol. In certain embodiments, the alcohol is iso-butanol. In certain embodiments, the alcohol is sec-butanol. In certain embodiments, the alcohol is and tert-butanol.

The carbonylation reaction may be carried out in a solvent, or a mixture of solvents (i.e., co-solvents). Solvents can be polar or non-polar, protic or aprotic. Any solvent may be used in the reactions described herein, and the reactions are not limited to particular solvents or combinations of solvents. Examples of solvents are provided herein. In certain embodiments, the reaction is carried out in a polar solvent, such as DMF. In certain embodiments, the reaction is carried out in a mixture of DMF and an alcohol (i.e., $R^2OH$). In certain embodiments, the reaction is carried out in the presence of DMF and methanol.

The carbonylation reaction may be carried out at any temperature. In certain embodiments, the reaction is carried out at or around room temperature (rt) (21° C. or 70° F.). In certain embodiments, the reaction is carried out at below room temperature (e.g., from 100° C. to 21° C.). In certain embodiments, a reaction is carried out at above room temperature. In certain embodiment, a reaction is carried out at 30, 40, 50, 60, 70, 80, 110, 120, 130, 140, or 150° C. In certain embodiments, a reaction is carried out at above 150° C.

In certain embodiments, the carbonylation is carried out in the presence of palladium, CO, $R^2OH$, and a phosphine. In certain embodiments, the carbonylation is carried out in the presence of palladium, CO, $R^2OH$, and a phosphine, in a polar solvent at around room temperature. In certain embodiments, the reaction is carried out in the presence of $Pd(OAc)_2$, CO, MeOH, and $Ph_3P$. In certain embodiments, the reaction is carried out in the presence of $Pd(OAc)_2$, CO, MeOH, and $Ph_3P$, in a polar solvent at around room temperature. In certain embodiments, the reaction is carried out in the presence of $Pd(OAc)_2$. CO, MeOH, and $Ph_3P$, in a DMF at around room temperature. In certain embodiments, the reaction is carried out in the presence of catalytic $Pd(OAc)_2$ (e.g., approximately 5 mol %), excess CO, excess MeOH, and catalytic $Ph_3P$ (e.g., approximately 14 mol %). In certain embodiments, the reaction is carried out in the presence of catalytic $Pd(OAc)_2$ (e.g., approximately 5 mol %), excess CO, excess MeOH, and catalytic $Ph_3P$ (e.g., approximately 14 mol %), in DMF at around room temperature.

In certain embodiments, the reaction is carried out in the presence of $Pd_2(dba)_3$, CO, MeOH, and dppf. In certain embodiments, the reaction is carried out in the presence of $Pd_2(dba)_3$, CO, MeOH, and dppf, in a polar solvent at around room temperature. In certain embodiments, the reaction is carried out in the presence of $Pd_2(dba)_3$, CO, MeOH, and dppf, in a polar solvent at above room temperature. In certain embodiments, the reaction is carried out in the presence of $Pd_2(dba)_3$, CO, MeOH, and dppf, in a DMF at around room temperature. In certain embodiments, the reaction is carried out in the presence of $Pd_2(dba)_3$, CO, MeOH, and dppf, in a DMF at above room temperature. In certain embodiments, the reaction is carried out in the presence of catalytic $Pd_2(dba)_3$ (e.g., approximately 1.5 mol %), excess CO, excess MeOH, and catalytic dppf (e.g., approximately 3 mol %). In certain embodiments, the reaction is carried out in the presence of catalytic $Pd_2(dba)_3$ (e.g., approximately 1.5 mol %), excess CO, excess MeOH, and catalytic dppf (e.g., approximately 3 mol %), in DMF at around room temperature. In certain embodiments, the reaction is carried out in the presence of catalytic $Pd_2(dba)_3$ (e.g., approximately 1.5 mol %), excess CO, excess MeOH, and catalytic dppf (e.g., approximately 3 mol %), in DMF at above room temperature.

The compound of Formula (II) may be isolated in any chemical yield. In certain embodiments, the compound is produced in from 1-10%, 10-20% 20-30%, 30-40%, 40-50%, 50-60%, 60-70%, 70-80%, 80-90%, or 90-100% yield. In certain embodiments, the chemical yield is greater than 10%, 20%, 30%, 40%, 50%, 60%, 70%, 80%, 90%, or 95%. In certain embodiments, the chemical yield is greater than 50%. In certain embodiments, the chemical yield is greater than 60%. In certain embodiments, the chemical yield is greater than 70%. In certain embodiments, the chemical yield is greater than 80%. In certain embodiments, the chemical yield is greater than 90%. In certain embodiments, the chemical yield is greater than 95%. In certain embodiments, the chemical yield is greater than 98%. In certain embodiments, the chemical yield is greater than 99%.

In certain embodiments, the compound of Formula (II) can be prepared and isolated in high chemical purity by a method described herein. In certain embodiments, the compound of Formula (II) is isolated in greater than 50%, 55%, 60%, 65%, 70%, 75%, 80%, 85%, 90%, 95%, 98%, or 99% purity. In certain embodiments, the compound of Formula (II) is isolated in greater than 90% purity. In certain embodiments, the compound of Formula (II) is isolated in greater than 95% purity. In certain embodiments, the compound of Formula (H) is isolated in greater than 98% purity. In certain embodiments, the compound of. Formula (H) is isolated in greater than 99% purity.

Methods described herein may further comprise one or more purification steps. For example, in certain embodiments, a compound produced by a method described herein may be purified by chromatography, extraction, filtration, precipitation, crystallization, or any other method known in the art. In certain embodiments, a compound or mixture is carried forward to the next synthetic step without purification (i.e., crude).

As defined herein, $X^1$ is halogen, optionally substituted sulfonate, optionally substituted phosphate. In certain embodiments, $X^1$ is halogen (e.g, —Br, —I, —Cl, —F). In certain embodiments, $X^1$ is optionally substituted phosphate. In certain embodiments, $X^1$ is optionally substituted sulfonate. In certain embodiments, $X^1$ is —$OSO_2$-alkyl. In certain embodiments, $X^1$ is mesylate (—$OSO_2CH_3$; "OMs"). In certain embodiments, $X^1$ is —$OSO_2$-aryl. In certain embodiments, $X^1$ is —$OSO_2Ph$. In certain embodiments, $X^1$ is tosylate (—$OSO_2C_6H_4p$-$CH_3$; "OTs"). In certain embodiments, $X^1$ is triflate (—$OSO_2CF_3$; "OTf"). In certain embodiments, $X^1$ is brosylate (—$OSO_2C_6H_4p$-Br; "OBs"), In certain embodiments, $X^1$ is nonaflate (—$OSO_2(CF_2)_3CF_3$; "ONf"). In certain embodiments, $X^1$ is nosylate (—$SO_2C_6H_4p$-$NO_2$ or —$SO_2C_6H_4o$-$NO_2$; "ONs"). In certain embodiments, $X^1$ is dansylate ("ODs").

In certain embodiments, $X^1$ is a leaving group. "Leaving group" is defined herein.

As defined herein, $R^1$ is optionally substituted alkyl, optionally substituted aryl, optionally substituted heteroaryl, optionally substituted carbocyclyl, optionally substituted heterocyclyl, or an oxygen protecting group. In certain embodiments, $R^1$ is optionally substituted alkyl. In certain embodiments, $R^1$ is optionally substituted aryl. In certain embodiments, $R^1$ is optionally substituted heteroaryl. In certain embodiments, $R^1$ is optionally substituted carbocyclyl. In certain embodiments, $R^1$ is optionally substituted heterocyclyl. In certain embodiments, $R^1$ is an oxygen protecting group. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-4}$ alkyl. In certain embodiments, $R^1$ is unsubstituted $C_{1-4}$ alkyl. In certain embodiments, $R^1$ is methyl, ethyl, n-propyl, iso-propyl, n-butyl, iso-butyl, sec-butyl, or tert-butyl. In certain embodiments, $R^1$ is methyl.

As defined herein, $R^2$ is optionally substituted alkyl, optionally substituted aryl, optionally substituted heteroaryl, optionally substituted carbocyclyl, optionally substituted heterocyclyl, or an oxygen protecting group. In certain embodiments, $R^2$ is optionally substituted alkyl. In certain embodiments, $R^2$ is optionally substituted aryl. In certain embodiments, $R^2$ is optionally substituted heteroaryl. In certain embodiments, $R^2$ is optionally substituted carbocyclyl. In certain embodiments, $R^2$ is optionally substituted heterocyclyl. In certain embodiments, $R^2$ is an oxygen protecting group. In certain embodiments, $R^2$ is optionally substituted $C_{1-6}$ alkyl. In certain embodiments, $R^2$ is unsubstituted $C_{1-6}$ alkyl. In certain embodiments, $R^2$ is optionally substituted $C_{1-4}$ alkyl. In certain embodiments, $R^2$ is unsubstituted $C_{1-4}$ alkyl. In certain embodiments, $R^2$ is methyl, ethyl, n-propyl, iso-propyl, n-butyl, iso-butyl, sec-butyl, or tert-butyl. In certain embodiments, $R^2$ is methyl.

In certain embodiments, $R^1$ and $R^2$ are the same. In certain embodiments, $R^1$ and $R^2$ are different. In certain embodiments, both $R^1$ and $R^2$ are methyl.

In certain embodiments, the compound of Formula (I) is of the formula:

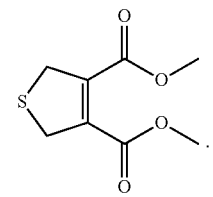

In certain embodiments, the compound of Formula (II) is of the formula:

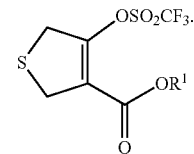

In certain embodiments, the compound of Formula (II) is of the formula:

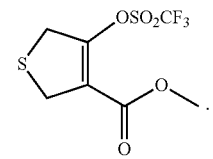

In certain embodiments, $X^1$ is a sulfonate, $R^1$ is optionally substituted alkyl, and the carbonylation is carried out in the presence of palladium, CO, $R^2OH$ ($R^2$ is optionally substituted alkyl), and a phosphine. In certain embodiments, $X^1$ is a sulfonate, $R^1$ is optionally substituted alkyl, and the carbonylation is carried out in the presence of palladium, CO, $R^2OH$ ($R^2$ is optionally substituted alkyl), and a phosphine, in a polar solvent at around room temperature. In certain embodiments, $X^1$ is a inflate, $R^1$ is optionally substituted alkyl, and the carbonylation is carried out in the presence of palladium, CO, $R^2OH$ ($R^2$ is optionally substituted alkyl), and a phosphine. In certain embodiments, $X^1$ is a triflate, $R^1$ is optionally substituted alkyl, and the carbonylation is carried out in the presence of palladium, CO, $R^2OH$ ($R^2$ is optionally substituted alkyl), and a phosphine, in an solvent at around room temperature. In certain embodiments, $X^1$ is triflate, $R^1$ is methyl, and the carbonylation is carried out in the presence of palladium, CO, MeOH, and a phosphine. In certain embodiments, $X^1$ is triflate, $R^1$ is methyl, and the carbonylation is carried out in the presence of palladium, CO, MeOH, and a phosphine, in a polar solvent at around room temperature. In certain embodiments, $X^1$ is triflate, $R^1$ is methyl, and the reaction is carried out in the presence of $Pd(OAc)_2$, CO, MeOH, and $Ph_3P$. In certain embodiments, $X^1$ is inflate, $R^1$ is methyl, and the reaction is carried out in the presence of $Pd(OAc)_2$, CO, MeOH, and $Ph_3P$, in a polar solvent at around room temperature. In certain embodiments, $X^1$ is inflate, $R^1$ is methyl, and the reaction is carried out in the presence of $Pd(OAc)_2$, CO, and $Ph_3P$, in DMF/MeOH at around room temperature. In certain embodiments, $X^1$ is triflate, $R^1$ is methyl, and the reaction is carried out in the presence of catalytic $Pd(OAc)_2$ (e.g., approximately 5 mol %), excess CO, excess MeOH, and catalytic $Ph_3P$ (e.g., approximately 14 mol %). In certain embodiments, $X^1$ is triflate, $R^1$ is methyl, and the reaction is carried out in the presence of catalytic $Pd(OAc)_2$ (e.g., approximately 5 mol %), excess CO, and catalytic $Ph_3P$ (e.g., approximately 14 mol. %), in DMF/MeOH at around room temperature.

Compounds

Also provided herein are compounds (i.e., intermediates) useful in the synthesis of cantharidin and analogs thereof. In certain embodiments, a compound provided herein is useful as a medicament (e.g, for the treatment of an infectious disease). For example, compounds of Formulae (IV), (V), and (VI), and pharmaceutically acceptable salts thereof, are useful for treating diseases or conditions in a subject in need thereof.

In one aspect, the present invention provides compounds of Formula (II):

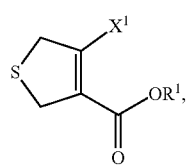

(II)

wherein:
X$^1$ is halogen, optionally substituted sulfonate, or optionally substituted phosphate;
R$^1$ is optionally substituted alkyl, optionally substituted aryl, optionally substituted heteroaryl, optionally substituted carbocyclyl, optionally substituted heterocyclyl, or an oxygen protecting group.

As defined herein, $X^1$ is halogen, optionally substituted sulfonate, optionally substituted phosphonate. In certain embodiments, $X^1$ is halogen (e.g, —Br, —I, —Cl). In certain embodiments, $X^1$ is optionally substituted phosphate. In certain embodiments, $X^1$ is optionally substituted sulfonate. In certain embodiments, $X^1$ is —$OSO_2$-alkyl. In certain embodiments, $X^1$ is mesylate (—$OSO_2CH_3$; "OMs"). In certain embodiments, $X^1$ is —$OSO_2$-aryl. In certain embodiments, $X^1$ is —$OSO_2Ph$. In certain embodiments, $X^1$ is tosylate (—$OSO_2C_6H_4p$-$CH_3$; "OTs"). In certain embodiments, $X^1$ is triflate (—$OSO_2CF_3$; "OTf"). In certain embodiments, $X^1$ is brosylate (—$OSO_2C_6H_4p$-Br; "OBs"), In certain embodiments, $R^1$ is nonaflate (—$OSO_2(CF_2)_3CF_3$; "ONf"). In certain embodiments, $X^1$ is nosylate (—$SO_2C_6H_4p$-$NO_2$ or —$SO_2C_6H_4o$-$NO_2$; "ONs"). In certain embodiments, $X^1$ is dansylate ("ODs").

In certain embodiments, $X^1$ is a leaving group. "Leaving group" is defined herein.

As defined herein, $R^1$ is optionally substituted alkyl, optionally substituted aryl, optionally substituted heteroaryl, optionally substituted carbocyclyl, optionally substituted heterocyclyl, or an oxygen protecting group. In certain embodiments, $R^1$ is optionally substituted alkyl. In certain embodiments, $R^1$ is optionally substituted aryl. In certain embodiments, $R^1$ is optionally substituted heteroaryl. In certain embodiments, $R^1$ is optionally substituted carbocyclyl. In certain embodiments, $R^1$ is optionally substituted heterocyclyl. In certain embodiments, $R^1$ is an oxygen protecting group. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-4}$ alkyl. In certain embodiments, $R^1$ is unsubstituted $C_{1-4}$ alkyl. In certain embodiments, $R^1$ is methyl, ethyl, n-propyl, iso-propyl, n-butyl, iso-butyl, sec-butyl, or tert-butyl. In certain embodiments, $R^1$ is methyl.

As defined herein, $R^2$ is optionally substituted alkyl, optionally substituted aryl, optionally substituted heteroaryl, optionally substituted carbocyclyl, optionally substituted heterocyclyl, or an oxygen protecting group. In certain embodiments, $R^2$ is optionally substituted alkyl. In certain embodiments, $R^2$ is optionally substituted aryl. In certain embodiments, $R^2$ is optionally substituted heteroaryl. In certain embodiments, $R^2$ is optionally substituted carbocyclyl. In certain embodiments, $R^2$ is optionally substituted heterocyclyl. In certain embodiments, $R^2$ is an oxygen protecting group. In certain embodiments, $R^2$ is optionally substituted $C_{1-6}$ alkyl. In certain embodiments, $R^2$ is unsubstituted $C_{1-6}$ alkyl. In certain embodiments, $R^2$ is optionally substituted $C_{1-4}$ alkyl. In certain embodiments, $R^2$ is unsubstituted $C_{1-4}$ alkyl. In certain embodiments, $R^2$ is methyl, ethyl, n-propyl, iso-propyl, n-butyl, iso-butyl, sec-butyl, or tert-butyl. In certain embodiments, $R^2$ is methyl.

In certain embodiments, $R^1$ and $R^2$ are the same. In certain embodiments, $R^1$ and $R^2$ are different. In certain embodiments, both $R^1$ and $R^2$ are methyl.

In certain embodiments, the compound of Formula (II) is of the formula:

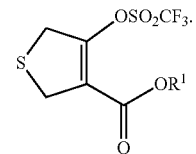

In certain embodiments, the compound of Formula (II) is of the formula:

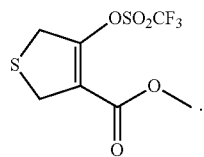

Also provided herein are compounds of Formula (IV):

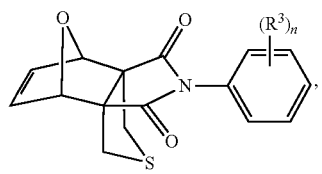

and pharmaceutically acceptable salts thereof, wherein:
n is 0, 1, 2, 3, 4, or 5;
each instance of R³ is independently hydrogen, halogen, —CN, —NO₂, —N₃, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)₂, or —SR$^S$;
each instance of R$^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
each instance of R$^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two R$^N$ on the same nitrogen are joined together with the intervening atoms to form optionally substituted heterocyclyl or optionally substituted heteroaryl;
each instance of R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

Also provided herein are compounds of Formula (V):

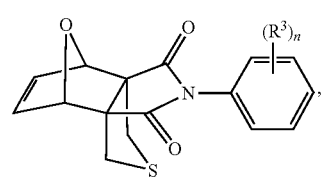

and pharmaceutically acceptable salts thereof, wherein:
n is 0, 1, 2, 3, 4, or 5;
each instance of R³ is independently hydrogen, halogen, —CN, —NO₂, —N₃, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)₂, or —SR$^S$;
each instance of R$^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
each instance of R$^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two R$^N$ on the same nitrogen are joined together with the intervening atoms to form optionally substituted heterocyclyl or optionally substituted heteroaryl;
each instance of R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

Also provided herein are compounds of Formula (III):

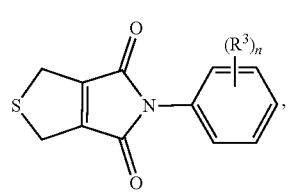

wherein:
n is 0, 1, 2, 3, 4, or 5;
each instance of R³ is independently hydrogen, halogen, —CN, —NO₂, —N₃, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)₂, or —SR$^S$;
each instance of R$^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
each instance of R$^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two R$^N$ on the same nitrogen are joined together with the intervening atoms to form optionally substituted heterocyclyl or optionally substituted heteroaryl;

each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

Also provided herein are compounds of Formula (VI):

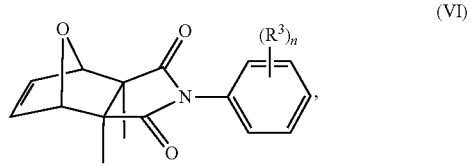

(VI)

wherein:
n is 0, 1, 2, 3, 4, or 5;
each instance of $R^3$ is independently hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)$_2$, or —SR$^S$;
each instance of $R^O$ is independently hydrogen, optionally substituted alkyl, optionally substituted carbocyclyl, optionally substituted heterocyclyl, optionally substituted aryl, optionally substituted heteroaryl, optionally substituted acyl, or an oxygen protecting group;
each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ on the same nitrogen are joined together with the intervening atoms to form optionally substituted heterocyclyl or optionally substituted heteroaryl; and
each instance of $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group.

As defined herein, n is 0, 1, 2, 3, 4, or 5. In certain embodiments, n is 0. In certain embodiments, n is 1. In certain embodiments, n is 2. In certain embodiments, n is 3. In certain embodiments, n is 4. In certain embodiments, n is 5.

As defined herein, each instance of $R^3$ is independently hydrogen, halogen, —CN, —NO$_2$, —N$_3$, optionally substituted alkyl, optionally substituted alkenyl, optionally substituted alkenyl, optionally substituted carbocyclyl, optionally substituted heterocyclyl, optionally substituted aryl, optionally substituted heteroaryl, optionally substituted acyl, optionally substituted sulfonyl, optionally substituted sulfinyl, —OR$^O$, —N(R$^N$)$_2$, or —SR$^S$. In certain embodiments, at least one instance of $R^3$ is hydrogen. In certain embodiments, at least one instance of $R^3$ is halogen. In certain embodiments, at least one instance of $R^3$ is —CN. In certain embodiments, at least one instance of $R^3$ is —NO$_2$. In certain embodiments, at least one instance of $R^3$ is —N$_3$. In certain embodiments, at least one instance of $R^3$ is optionally substituted alkyl. In certain embodiments, at least one instance of $R^3$ is optionally substituted alkenyl. In certain embodiments, at least one instance of $R^3$ is optionally substituted alkynyl. In certain embodiments, at least one instance of $R^3$ is optionally substituted carbocyclyl. In certain embodiments, at least one instance of $R^3$ is optionally substituted heterocyclyl. In certain embodiments, at least one instance of $R^3$ is optionally substituted aryl. In certain embodiments, at least one instance of $R^3$ is optionally substituted heteroaryl. In certain embodiments, at least one instance of $R^3$ is optionally substituted acyl. In certain embodiments, at least one instance of $R^3$ is optionally substituted sulfonyl. In certain embodiments, at least one instance of $R^3$ is optionally substituted sulfinyl. In certain embodiments, at least one instance of $R^3$ is —OR$^O$. In certain embodiments, at least one instance of $R^3$ is —N(R$^N$)$_2$. In certain embodiments, at least one instance of $R^3$ is —SR$^S$.

Pharmaceutical Compositions, Kits, and Administration

The present disclosure provides pharmaceutical compositions comprising a compound of Formula (IV), (V), or (VI), or a pharmaceutically acceptable salt thereof, and a pharmaceutically acceptable excipient. In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating an infectious disease or skin condition in a subject in need thereof.

Pharmaceutical compositions described herein can be prepared by any method known in the art of pharmacology. In general, such preparatory methods include bringing the compound described herein (i.e., the "active ingredient" or "active compound") into association with a carrier or excipient, and/or one or more other accessory ingredients, and then, if necessary and/or desirable, shaping, and/or packaging the product into a desired single- or multi-dose unit. In certain embodiments, the "active ingredient" or "active compound" is a compound of Formula (IV), (V), or (VI), or a pharmaceutically acceptable salt thereof.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. In certain embodiments the composition may comprise between 0.1% and 0.100% (w/w) active ingredient.

In some cases, a composition can comprise at least about 50% (w/v) of active compound, at least about 10% (w/v) of active compound, at least about 5% (w/v) of active compound, at least about 1% (w/v) of active compound, at least about 0.75% (w/v) of active compound, at least about 0.5% (w/v) of active compound, at least about 0.1% (w/v) of active compound, at least about 0.01% (w/v) of active compound, or at least about 0.001% (w/v) of active compound. The active compound may be present in an amount between about 0.001% and 50% by weight, or between about 1% and about 10% by weight, or between about 0.001% and 1% by weight.

A pharmaceutical composition can have an active compound concentration (milligram (mg) active ingredient/milliliter (mL) formulation) of about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL, 6.0 mg/mL, 6.1 mg/mL, 6.2 mg/mL, 6.3 mg/mL, 6.4 mg/mL, 6.5 mg/mL, 6.6 mg/mL, 6.7 mg/mL, 6.8 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, 8.9 mg/mL, 9.0 mg/mL, 9.1 mg/mL, 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL, 10.1 mg/mL, 10.2 mg/mL, 10.3 mg/mL, 10.4 mg/mL, 10.5 mg/mL, 10.6 mg/mL, 10.7 mg/mL, 10.8 mg/mL, 10.9 mg/mL, 11.0 mg/mL, 11.1 mg/mL, 11.2 mg/mL, 11.3 mg/mL, 11.4 mg/mL, 11.5 mg/mL, 11.6 mg/mL, 11.7 mg/mL, 11.8 mg/mL, 11.9 mg/mL, 12.0 mg/mL, 12.1 mg/mL, 12.2 mg/mL, 12.3 mg/mL, 12.4 mg/mL, 12.5 mg/mL, 12.6 mg/mL, 12.7 mg/mL, 12.8 mg/mL, 12.9 mg/mL, 13.0 mg/mL, 13.1 mg/mL, 13.2 mg/mL, 13.3 mg/mL, 13.4 mg/mL, 13.5 mg/mL, 13.6 mg/mL, 13.7 mg/mL, 13.8 mg/mL, 13.9 mg/mL, 14.0 mg/mL, 14.1 mg/mL, 14.2 mg/mL, 14.3 mg/mL, 14.4 mg/mL, 14.5 mg/mL, 14.6 mg/mL, 14.7 mg/mL, 14.8 mg/mL, 14.9 mg/mL, 15.0 mg/mL, 15.5 mg/mL, 16.0 mg/mL, 16.5 mg/mL, 17.0 mg/mL, 17.5 mg/mL, 18.0 mg/mL, 18.5 mg/mL, 19.0 mg/mL, 19.5 mg/mL, or 20.0 mg/mL. In some examples, the active ingredient concentration is an amount of 0.5 milligrams (mg) to 20 mg per milliliter (ml), or 1 mg to 10 mg per ml.

As an alternative, a pharmaceutical composition can have an active ingredient concentration (mg active ingredient/mL formulation) of at least about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL, 6.0 mg/mL, 6.1 mg/mL, 6.2 mg/mL, 6.3 mg/mL, 6.4 mg/mL, 6.5 mg/mL, 6.6 mg/mL, 6.7 mg/mL, 6.8 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, 8.9 mg/mL, 9.0 mg/mL, 9.1 mg/mL, 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL, 10.1 mg/mL, 10.2 mg/mL, 10.3 mg/mL, 10.4 mg/mL, 10.5 mg/mL, 10.6 mg/mL, 10.7 mg/mL, 10.8 mg/mL, 10.9 mg/mL, 11.0 mg/mL, 11.1 mg/mL, 11.2 mg/mL, 11.3 mg/mL, 11.4 mg/mL, 11.5 mg/mL, 11.6 mg/mL, 11.7 mg/mL, 11.8 mg/mL, 11.9 mg/mL, 12.0 mg/mL, 12.1 mg/mL, 12.2 mg/mL, 12.3 mg/mL, 12.4 mg/mL, 12.5 mg/mL, 12.6 mg/mL, 12.7 mg/mL, 12.8 mg/mL, 12.9 mg/mL, 13.0 mg/mL, 13.1 mg/mL, 13.2 mg/mL, 13.3 mg/mL, 13.4 mg/mL, 13.5 mg/mL, 13.6 mg/mL, 13.7 mg/mL, 13.8 mg/mL, 13.9 mg/mL, 14.0 mg/mL, 14.1 mg/mL, 14.2 mg/mL, 14.3 mg/mL, 14.4 mg/mL, 14.5 mg/mL, 14.6 mg/mL, 14.7 mg/mL, 14.8 mg/mL, 14.9 mg/mL, 15.0 mg/mL, 15.5 mg/mL, 16.0 mg/mL, 16.5 mg/mL, 17.0 mg/mL, 17.5 mg/mL, 18.0 mg/mL, 18.5 mg/mL, 19.0 mg/mL, 19.5 mg/mL, or 20.0 mg/mL. In some situations, the formulation can have an active ingredient concentration that is less than or equal to about 40 mg/mL, 30 mg/mL, 20 mg/mL, 10 mg/mL, 5 mg/mL, or 1 mg/mL.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g, carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g, Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are topical in nature.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose or multiple doses.

A composition may be delivered to a subject (e.g., to a skin area of the subject having or suspected of having a wart or cutaneous lesion) from once a day to once a month or more. As an alternative or in addition to, a composition may be delivered to a subject from once a day to once a week. As an alternative or in addition to, a composition may be delivered to a subject at least once a day, once every two days, once every three days, once every four days, once every five days, once every six days, once a week, once every 10 days, once every two weeks, once every three weeks, once a month, once every two months, once every three months, once every four months, once every five months, once every six months, once a year, or more. As an alternative or in addition to, a composition may be delivered to a subject at least once a day, or twice a day, or three times per day, or four times per day, or five times per day, or six times per day, or seven times per day, or eight times per day, or nine times per day, or ten times per day, or eleven times per day, or twelve times per day, or thirteen times per day, or fourteen times per day, or fifteen times per day, or sixteen times per day, or seventeen times per day, or eighteen times per day, or nineteen times per day, or twenty times per day, or twenty one times per day, or twenty two times per day, or twenty three times per day, or twenty four times per day. As an alternative or in addition to, a composition may be delivered to a subject as soon as skin begins to epithelialize after previous treatment. As an alternative or in addition to, a composition may be delivered to a subject as soon as skin has partially epithelized after previous treatment. As an alternative or in addition to, a composition may be delivered to a subject as soon as skin has fully epithelized after previous treatment.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g, activity (e.g., potency and/or efficacy) in treating a disease in a subject in need thereof, in preventing a disease in a subject in need thereof, in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g, combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)).

A pharmaceutical composition of the present disclosure can contain other topical agents. Topical agents include, but are not limited to, local anesthetics, local analgesics, antimicrobial agents, microbicidal agents, disinfectants, antiseptics, antibiotics, bactericidal agents, bacteriostatic agents, cleansing agents, anti-inflammatory agents, anti-infective agents (e.g., gentian violet), emollients, astringents, anti-acne agents, anti-virals, anti-fungals, fungicides, anti-psoriasis agents, antiparasitics, steroid hormones such as corticosteroids. Examples of topical agents include, but are not limited to, Altabax (retapamulin), Amevive (alefacept), Avita gel, Bactroban cream, benzamycin, erythromycin, botox, cefazolin, dextrose, chloraprep (chlorhexidine gluconate), clindamycin phosphate, condylox (pokofilox), desonate (desonide), differin (adapalene), Dynabac, Elide, Erivedge (vismodegib), Estrostep, norethindrone acetate, ethinyl estradiol, Extina (ketoconazole), Fiacea (azelaic acid), Finevin, Firazyr (icatibant), Gralise (gabapentin), Fiorizant (gapabentin enacarbil), hydrochloric acid, hydrogen peroxide, Iamin, Invanz, Iontocaine, IvyBlock, Klaron (sodium sulfacet amide), Lamisil (terbinafine hydrochloride), LaViv (azficel-T), Lustra, Luxiq (betamethasone valerate), Mentax (butenafine HCl), MetroLotion, Minoxidil, Noritate, nitric acid, Omnicef, Ortho Tri-Cyclee, norgestimate, Picato (ingenol mebutate), Propecia, Protopic (tacrolimus), Condylox (podophotoxin), Regranex (becaplermin), Renova, tratinoin, salagen, sandalwood oil, salicylic acid, Sklice (ivermectin), Stelara (ustkinumab), Sulfamylon, Sylatron (peg interferon alpha-2b), Tazorac, Teflaro (ceftaroline fosamil), Thalomid, Trichloroacetic acid, Tygacil (tigecycline), Veltin (clindamycin phosphate), tretinoin, Veregen (green tea sincatechins), Verdeso (desonide), Vibativ (telavancin), Vibativ (telavancin), Xyzal (levocetirizine dihydrochloride), Yervoy (ipilimumab), Zelboraf (vemurafenib), and Zyclara (imiquimod).

Also encompassed by the disclosure are kits (e.g, pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., infectious disease or skin condition) in a subject in need thereof. In certain embodiments, the kits are useful for preventing a disease (e.g., infectious disease or skin condition) in a subject in need thereof. In certain embodiments, the kits are useful for reducing the risk of developing or contracting a disease (e.g., infectious disease or skin condition) in a subject in need thereof. In certain embodiments, a kit described herein further includes instructions for using the kit. A kit described herein may also include information as required by a regulatory agency such as the U.S. Food and Drug Administration (FDA). In certain embodiments, the information included in the kits is prescribing information.

In certain embodiments, the active ingredient in a pharmaceutical composition is present in high-purity with respect to the active ingredient (i.e., not taking into account other active ingredients, excipients, carriers, solvents, etc.). In certain embodiments, the purity is greater than 50%, 55%, 60%, 65%, 70%, 75%, 80%, 85%, 90%, 95%, 98%, or 99% with respect to the active ingredient. In certain embodiments, the purity is greater than 90% with respect to the active ingredient. In certain embodiments, the purity is greater than 95% with respect to the active ingredient. In certain embodiments, the purity is greater than 98% with respect to the active ingredient. In certain embodiments, the purity is greater than 99% with respect to the active ingre-dient. In certain embodiments, the purity is greater than 99.1%. 99.2%, 99.3%, 99.4%, 99.5%, 99.6%, 99.7%, 99.8%, or 99.9% purity.

Methods of Treatment and Use

Compounds provided herein may have biological activity and therefore can be useful in the treatment of diseases or conditions (e.g., infectious diseases, skin conditions).

Provided herein is a method of treating a disease or condition in a subject, the method comprising administering to the subject an effective amount of a compound of Formula (IV), (V), or (VI), or a pharmaceutically acceptable salt thereof, or a pharmaceutical composition thereof. The present invention also provides compounds of Formula (IV), (V), and (VI), and pharmaceutically acceptable salts thereof, and pharmaceutical compositions thereof, for use in treating diseases and conditions in a subject. The present invention also provides uses of compounds of Formulae (IV), (V), and (VI), or pharmaceutically acceptable salts thereof, and pharmaceutical compositions thereof, for the manufacture of medicaments for treating diseases or conditions in a subject. In certain embodiments, the disease is an infectious disease. In certain embodiments, the conditions is a skin condition.

In certain embodiments, the disease is an infectious disease. An "infectious disease" refers to any disease caused by a pathogen (i.e., pathogenic microorganisms). An infectious disease may be caused by bacteria, viruses, parasites, or fungi. An infectious disease can be a microbial infection. A "microbial infection" refers to an infection with a microorganism, such as a fungus, bacteria or virus. In certain embodiments, the microbial infection is an infection with a fungus, i.e., a fungal infection. In certain embodiments, the microbial infection is an infection with a virus, i.e., a viral infection. In certain embodiments, the microbial infection is an infection with a bacteria, i.e., a bacterial infection. Various microbial infections include, but are not limited to, skin infections, GI infections, urinary tract infections, genito-urinary infections, sepsis, blood infections, and systemic infections. In certain embodiments, the infectious disease is a bacterial infection. In certain embodiments, the infectious disease is a viral infection. In certain embodiments, the infectious disease is a microbial infection.

In certain embodiments, a compound described herein is useful in treating an infectious disease or skin condition. Examples of infectious diseases and skin conditions include, but are not limited to, Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer, Bowen's disease, Breast cancer. Buschke-Ollendorff syndrome, Cervical cancer, Cervical dysplasia, Cherry angiomas, Chondrodermatitis nodularis chronica helicis, Common warts, Cutaneous endometriosis, Cutaneous Leukemia, Cutaneous Lymphoma, Cutaneous meningioma, Cutaneous myxoma, Darier's disease, Dermal dendrocyte hamartoma, dermatofibroma, Dermatofibrosarcoma protuberans, Eccrine angiomatous hamartoma, Ectodermal dysplasia, Epidermal inclusion cysts, Epidermal Naevi, Epithelioid cell histiocytoma, Familial myxovascular fibromas, Fungal skin disease, Granular cell tumor, Glucaonoma syndrome, Genital warts, ichthyosis, idiopathic guttate hypomelanosis, Infantile acropustulosis, Infantile fibromatosis, Kaposi's sarcoma, Keloid, Keratoacanthoma, Keratocyst, Knuckle pads, Lentigo, Melanoma, Microvenular hemangioma, Molluscum contagiousum, Morton's neuroma, Multifocal lymphangioendotheliomatosis, Multinucleate cell angiohistocytoma, Multiple cutaneous leiomyomas, Mycosis fungoides, Neuroma cutis, Neurothekeoma, Nevus flammeus, Nevus lipomatosus superficialis, Pachydermodactyly, Palisaded encapsulated neuroma, Parasitic skin diseases, Pityriasis ruba pilaris, Piloleiomyomas, Plantar warts, Plexiform fibrohistiocytic tumor, Porokeratotic eccrine ostial and Dermal duct nevus, Progressive nodular histiocytoma Psoriasis, Porokeratosis, Seborrhoeic dermatitis, Seborrhoeic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis, Zosteriform metastasis, Benign epidermal cysts, Birthmarks, Calluses, Corns, Eczema, Freckles, Moles, Pigmentation disorders, Drug induced hyperpigmentation, Dyschromatosis symmetrica hereditaria, Dyschromatosis universalis hereditaria, Familial progressive hyperpigmentation, Galli-Galli disease, Hemosiderin hyperpigmentation, Idiopathic guttate hypomelanosis, Iron metallic discoloration, leukoderma, Melasma, Mukamel syndrome, Necklace of Venus, Nevus anemicus, Nevus depigmentosus, Pallister-Killian syndrome, Phylloid hypomelanosis, Piebaldism, Pigmentatio reticularis faciei et colli, Pilar Cysts, Pityriasis alba, Poikiloderma of Civatte, Poikiloderma vasculare atrophicans, Postinflammatory hyperpigmentation, Progressive macular hypomelanosis, Pruritus, Reticular pigmented anomaly of the flexures, Reticulate acropigmentation of Kitamura, Riehl melanosis, Shah-Waardenburg syndrome, Shiitake mushroom dermatitis, Tar melanosis, Titanium metallic discoloration, Transient neonatal pustular melanosis, Vagabonds leukomelanoderma, Vasospastic macules, Wende-Bauckus syndrome, X-linked reticulate pigmentary disorder, Yemenite deaf-blind hypopigmentation syndrome, Scars, Skin tags, Tattoo removal, and Vitiligo.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, 2$^{nd}$ Edition, Wiley-VCH Publishers, Inc., New York, 1999; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H., *Tables of Resolving Agents and Optical Resolutions p.* 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

"Sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

"Sulfonyl" refers to the group —S(=O)R$^{aa}$, wherein R$^{aa}$ is as defined herein.

The term "phosphoryl" refers to a group selected from —P(=O)(OR$^{cc}$)$_2$, —P(=O)(R$^{aa}$)$_2$, and —P(=O)(N(R$^{bb}$)$_2$)$_2$, wherein R$^{aa}$, R$^{bb}$, and R$^{cc}$ are as defined herein.

"Sulfonate" refers to a group selected from —OSO$_2$N(R$^{bb}$)$_2$, —OSO$_2$R$^{aa}$, and —OSO$_2$OR$^{aa}$, wherein R$^{aa}$ and R$^{bb}$ are as defined herein. Examples of sulfonate groups include, but are not limited to, —OSO$_2$Ph, tosylate (—OSO$_2$C$_6$H$_4$p-CH$_3$; "OTs"), triflate (—OSO$_2$CF$_3$; "OTf"); brosylate (—OSO$_2$C$_6$H$_4$p-Br; "OBs"), nonaflate (—OSO$_2$(CF$_2$)$_3$CF$_3$; "ONf"), nosylate (—SO$_2$C$_6$H$_4$p-NO$_2$ or —SO$_2$C$_6$H$_4$o-NO$_2$; "ONs"), and dansylate ("ODs").

"Phosphate" refers to a group selected from —O(P)(R$^{aa}$)$_2$, —O(P)(OR$^{cc}$)R$^{aa}$, —O(P=O)(OR$^{cc}$)$_2$, —O(P=O)(NR$^{bb}$)$_2$ wherein R$^{aa}$, R$^{bb}$, and R$^{cc}$ are as defined herein.

The term "acyl" refers to a group having the general formula —C(=O)R$^{X1}$, —C(=S)N(R$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —R$^{aa}$, —OR$^{cc}$, or —OR$^{bb}$; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas.

The term "halo" or "halogen" refers to fluorine (fluoro, —F), chlorine (chloro, —C$_1$), bromine (bromo, —Br), or iodine (iodo, —I).

When a range of values is listed, it is intended to encompass each value and sub-range within the range. For example, "C$_{1-6}$ alkyl" is intended to encompass, C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$ alkyl.

The term "alkyl" refers to a radical of a straight-chain or branched saturated hydrocarbon group having from 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-4}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or 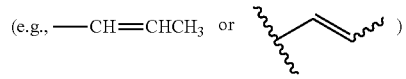 )

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl."). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl."). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl."). Exemplary C$_{3-6}$ carbocyclyl groups include, without limitation, cyclopropyl (C$_3$), cyclopropenyl (C$_3$), cyclobutyl (C$_4$), cyclooctenyl (C$_4$), cyclopentyl (C$_5$), cyclopentenyl (C$_5$), cyclohexyl (C$_6$), cyclodecenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl." is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$, cycloalkyl"). In some embodiments, a cycloalkyl group has 4 to 6 ring carbon atoms ("$C_{4-6}$, cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or Spiro ring system such as a bicyclic system ("bicyclic heterocyclyl") or tricyclic system. ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b] pyranyl, 5,7-dihydro-4H-thieno[2,3-c]pyranyl, 2,3-dihydro-1H-pyrrolo[2,3-b]pyridinyl, 2,3-dihydrofuro[2,3-b] pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 Z electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g, having 6, 10, or 14 it electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g, 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^a$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, NR$^{Fr}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{f}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(RC$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(RC$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, Ciao carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$ alkenyl, heteroC$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alky))$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl); —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC =O)NH($C_{1-6}$ alkyl), —NHC(=O)NH$_2$, —C(=NH)O($C_{1-6}$ alkyl), —OC(=NH)($C_{1-6}$ alkyl), —OC(=NH)OC$_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(=NH)NH($C_{1-6}$ alkyl), —OC(=NH)NH$_2$, —NHC(=NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$($C_{1-6}$ alkyl), —SO$_2$O($C_{1-6}$ alkyl), —OSO$_2$($C_{1-6}$ alkyl), —SO($C_{1-6}$ alkyl), —Si($C_{1-6}$ alkyl)$_3$, —OSi($C_{1-6}$ alkyl)$_3$, —C(=S)N($C_{1-6}$ alky))$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, carbon atom substituents include: halogen, —CN, —NO$_2$, —N$_3$, —SO$_2$H, —SO$_3$H, —OH, —OC$_{1-6}$ alkyl, —ON($C_{1-6}$ alkyl)$_2$, —N($C_{1-6}$ alkyl)$_2$, N($C_{1-6}$ alkyl)$_3^+$X$^-$, —NH($C_{1-6}$ alkyl)$_2^+$X$^-$, —NH$_2$($C_{1-6}$ alkyl)$^+$X$^-$, —NH$_3^+$X$^-$, —N(O$C_{1-6}$ alkyl)($C_{1-6}$ alkyl), —N(OH)($C_{1-6}$ alkyl), —NH(OH), —SH, —SC$_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), N($C_{1-6}$ alkyl)C(=O)($C_{1-6}$ alkyl), —NHCO$_2$($C_{1-6}$ alkyl), —NHC(=O)N($C_{1-6}$ alkyl)$_2$, NHC(=O)NH($C_{1-6}$ alkyl), —NHC(=O)NH$_2$, —C(=NH)O($C_{1-6}$ alkyl), —OC(=NH)($C_{1-6}$ alkyl), —OC(NH)OC$_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(=NH)NH($C_{1-6}$ alkyl), —OC(=NH)NH$_2$, —NHC(—NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$($C_{1-6}$ alkyl), —SO$_2$O($C_{1-6}$ alkyl), —OSO$_2$($C_{1-6}$ alkyl), —SO($C_{1-6}$ alkyl), —Si($C_{1-6}$ alkyl)$_3$, —OSi($C_{1-6}$ alkyl)$_3$—C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl. —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form or =S; wherein $X^-$ is a counterion.

A "counterion" or "anionic counterion" is a negatively—we are much more likely to form cationic salts of our mono and di carboxylic acids like Na, K, NR$_4$ salts—charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$, NO$_3^-$, ClO$_4^-$, OH$^-$, H$_2$PO$_4^-$, HCO$_3^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4$]$^-$, B(C$_6$F$_5$)$_4^-$, BPh$_4^-$, Al(OC(CF$_3$)$_3$)$_4$, and carborane anions (e.g., CB$_{11}$H$_{12}$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Any compound provided herein, or used in a method provided herein, can be provided and/or used as a salt thereof. As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "leaving group" is given its ordinary meaning in the art of synthetic organic chemistry and refers to an atom or a group capable of being displaced by a nucleophile. See, for example, Smith, *March Advanced Organic chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesuifonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^3$a, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 5$^{th}$ edition, John Wiley & Sons, 2014, incorporated herein by reference.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. In certain embodiments, a reaction described herein is carried out in an ionic liquid. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), dimethyl sulfone, sulfolane, nitromethane, 1-octanol, pentane, 3-pentanone, 1-propanol, 2-propanol, pyridine, tetrachloroethylene, tetrahydrofuran (THF), 2-methyltetrahydrofuran, toluene, trichlorobenzene, 1,1,2-trichlorotrifluoroethane, 2,2,4-trimethylpentane, trimethylamine, triethylamine, N N-diisopropylethylamine, diisopropylamine, water, o-xylene, and p-xylene.

The term "catalysis," "catalyze," or "catalytic" refers to the increase in rate of a chemical reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have lower activation energy (rate-limiting free energy of activation) than the corresponding uncatalyzed reaction, resulting in a higher reaction rate at the same temperature. Catalysts may affect the reaction environment favorably, bind to the reagents to polarize bonds, form specific intermediates that are not typically produced by a uncatalyzed reaction, or cause dissociation of reagents to reactive forms.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

Examples

In order that the invention described herein may be more fully understood, the following examples are set forth. It should be understood that these examples are for illustrative purposes only and are not to be construed as limiting this invention in any manner.

The methods provided herein may be applied to the synthesis of cantharidin, for example, as shown in Scheme 4.

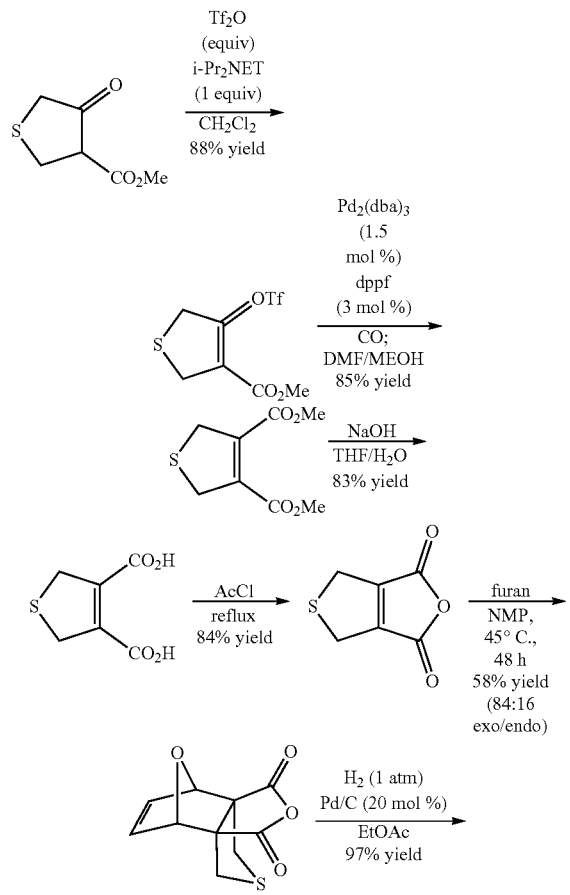

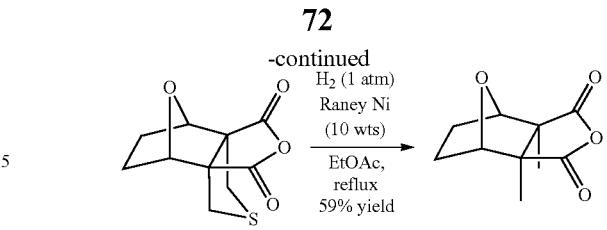

As described herein, studies into the industrial scale preparation of cantharidin led to the discovery of surprising and unprecedented Diels-Alder reaction conditions for reacting furan and Compound (2) to yield key the synthetic tetracyclic intermediate, Compound (1).

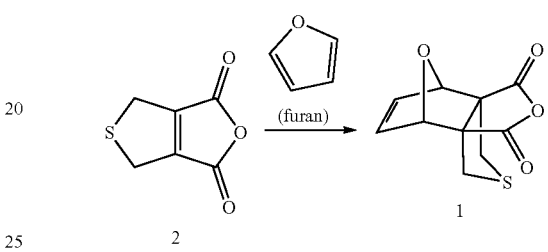

Starting with the work reported by Dauben in the 1980s (See, e.g., *JACS*, 102, 6893(1980) and JOG, 50, 2576-2578 (1985)), it was presumed that this Diels-Alder cycloaddition would require exotic, highly demanding reaction conditions. This assumption arose from the expected steric congestion that would be generated in formation of Compound (1). Although not the same molecule, the work of Bruchhausen in 1928 demonstrated that dehydrocantharidin spontaneously underwent a retro Diels-Alder reaction to alleviate this congestion. In addition, Diels and Alder reported that the forward reaction of furan and dimethyl maleic anhydride to form dehydrocantharidin was not possible (see, e.g., *BER.* 62, 554-562 (1929)). Recognizing this facile retro Diels-Alder liability, Dauben used exceedingly high pressures (>7 kbar) to force the electrocyclic addition of Compound (2) to Compound (1) in a volume contraction-driven process. Subsequently Grieco (see, e.g., *JACS*, 112, 4595-459 (1990)) used highly concentrated ethereal solutions of the Lewis acid, lithium perchlorate (5 M), to catalyze the reaction as well as create a high salt content-driven effect ("high" internal solvent pressure) to force adduct (1) to form.

Unfortunately, neither the Dauber nor the Grieco conditions are viable large-scale production methods for a commercial product. The super high pressures used in the Dauben protocol or the use of ethereal perchlorate solutions of the Grieco method are both subject to significant explosion risks which are unacceptable to manufacturers. A second Grieco method using lithium trifluoromethanesulfonimide in either diethyl ether or acetone also yielded the desired adduct (1) but at a high reagent cost. More significantly, there was a serious erosion of the favorable exo-endo ratio leading to a much poorer yield of Compound (1).

It was discovered that other Lewis acids could replace the lithium Lewis acids in the Grieco procedure (International Publication No. WO 2016/100732, published Jun. 23, 2016, the entire contents of which is incorporated herein by reference). These studies demonstrated that the exo/endo ratios were significantly improved, and the product yields were viable.

However, it was recently discovered that mixing a solution of the two reactions in a polar solvent like acetonitrile, NMP, DMPU, and acetone solvents with modest warming gave a 64% conversion to Compound (1) with a very favorable 84:16 ratio of exo-endo isomers (using NMP). Isolation of the desired product Compound (1) could readily be accomplished simple basic work-up to remove the starting material for reuse and a simple recrystallization procedure to remove the minor undesired endo isomer. The isolated yield for this reaction is 58% at 99% purity. The fact that such simple reaction conditions are all that is required for successful formation of adduct (1) from Compound (2) and furan is totally unexpected based on 37 years of precedent. The success of these specific Diels-Alder conditions was not predicted for these two substrates and are quite suitable for industrial-scale production of cantharidin.

4

5

Compound (5) is a key intermediate in a synthesis of cantharidin. Numerous reports of its synthesis have appeared in the literature but are unworkable (use of cyanide or nitromethane) and/or too expensive for industrial production of Compound (5). In a process never reported before, intermediate (4) (a compound of Formula (II) wherein $X^1$ is a sulfonate) can be carboxylated with palladium-catalyzed addition of carbon monoxide to give the key synthetic intermediate (5). This single step process gives a 85% yield of Compound (5) despite the presence of the typical palladium catalyst poison, sulfur, in both the starting material and product. The presence of the presumably catalyst toxic sulfur is most likely the reason why this conversion has not been reported to date.

Experimental Procedures

Preparation of [3-(methoxycarbonyl)-4-oxotetrahydro-3-thienyl]lithium

Methyl acrylate (9.16 mL, 102 mmol) is added to a mixture of methyl mercaptoacetate (8.42 mL, 94.2 mmol) and piperidine (0.186 mL, 1.88 mmol) at room temperature over 30 min. When addition is complete, the mixture is stirred at room temperature for 30 min. In a separate flask, lithium (0.654 g, 94.2 mmol) is dissolved in 40 ml of MeOH under $N_2$. The methyl acrylate mixture is added to the lithium methoxide solution at room temperature under $N_2$ over 1 hr. When addition is complete, the mixture is warmed to reflux for 6 hrs. The MeOH is evaporated and the resulting thick oil is taken up in 30 ml of ice cold water. The resulting mixture is stirred with ice bath cooling for 1 hr. The solid that forms is collected by filtration and dried with a $N_2$ press for 2 hrs. The solid is suspended in MTBE (20 ml, 2 vol) and stirred at room temperature for 2 hrs. The solid is collected by filtration and dried with a $N_2$ press at room temperature for 2 hrs to give [3-(methoxycarbonyl)-4-oxotetrahydro-3-thienyl]lithium (11.0 g; Yield=70.3%) as a light yellow solid.

Preparation of methyl 4-oxotetrahydrothiophene-3-carboxylate

[3-(Methoxycarbonyl)-4-oxotetrahydro-3-thienyl]lithium (17.7 g, 106 mmol) is suspended in 100 mL of water and the suspension was acidified to pH 5 by addition of 1.0N HCl. The resulting mixture is extracted with 3×50 ml of $CH_2Cl_2$. The combined $CH_2Cl_2$ layers are dried over $Na_2SO_4$ and evaporated to give methyl 4-oxotetrahydrothiophene-3-carboxylate (14 g; Yield=82%) as a light yellow oil.

Preparation of methyl 4-{[(trifluoro(methyl)sulfonyl]oxy}-2,5-dihydrothiophene-3-carboxylate

5

6

A solution of methyl 4-oxotetrahydrothiophene-3-carboxylate (62.0 g, 387 mmol), methylene chloride (310 mL, 4800 mmol) (5 volumes), and N,N-diisopropylethylamine (74.2 mL, 426 mmol) is cooled to −30° C. under $N_2$. To the solution is added trifluoromethanesulfonic anhydride (68.4 mL, 406 mmol) at a rate that maintains the reaction mixture at or below −20° C. When addition is complete, the mixture is stirred at −30° C. for ½ hour at which point TLC in $CH_2Cl_2$ showed no starting material remained. The reaction was quenched by addition of 300 ml of water and the layers were separated. The $CH_2Cl_2$ layer was extracted with 200 ml of water and dried over $Na_2SO_4$. Evaporation of the solvent gave 172 g of a dark oil. The oil was taken up in 200 ml of 1:1 $CH_2Cl_2$/hexane and adsorbed onto a silica gel pad (258 g, 1.5 weights). The pad was eluted with 3 L of 1:1 $CH_2Cl_2$/hexane. Evaporation of the filtrate and drying under high vacuum at room temperature overnight gave 101 g of methyl 4-{[(trifluoromethyl)sulfonyl]oxy}-2,5-dihydrothiophene-3-carboxylate (101 g; Yield=89%) as a light yellow oil.

Preparation of dimethyl 2,5-dihydrothiophene-3,4-dicarboxylate

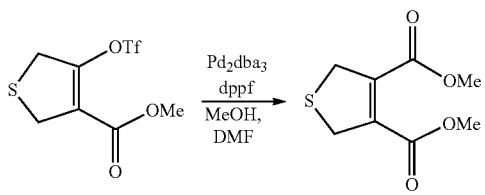 [SMILES: COC(=O)C1=C(OS(=O)(=O)C(F)(F)F)CSC1 ; "Pd2dba3dppf" ; COC(=O)C1=C(C(=O)OC)CSC1]

An oil bath was pre-heated to 50° C. A mixture of methyl 4-{[(trifluoromethyl)sulfonyl]oxy}-2,5-dihydrothiophene-3-carboxylate (15.58 g, 53.31 mmol), tris(dibenzylideneacetone)dipalladium(0) (742 mg, 0.810 mmol), and 1,1'-Bis(diphenylphosphino)ferrocene (888 mg, 1.60 mmol) were suspended in methanol (10.2 mL, 252 mmol) and DMF (5.1 mL, 66 mmol) in a 100 mL pressure tube fitted with a pressure gauge. The tube was pressurized with 40 psi of CO and the CO was allowed to vent. The purging process was repeated once more and then the reaction was pressurized again with 40 psi of CO. The tube was placed in the pre-heated oil bath and was stirred for 24 h. After 24 h, HPLC analysis showed complete conversion of the starting material. The reaction mixture was transferred to a round-bottom flask and concentrated in vacuo to remove methanol. The thick residual mixture was filtered through a pad of Magnesol (60 g) and the filter cake was washed with TBME (400 mL). The filtrate was concentrated in vacuo to afford the product (13.05 g; Yield=84.73%; Purity=70%; as an orange oil). If the rate of the reaction is slow, additional $Pd_2(dba)_3$ and dppf can be added. $^1$H NMR was acquired in $CDCl_3$ w/p-xylene as an internal standard. On a 3.0 g scale, this procedure gave an 85% yield at 72% purity. On a 19.4 g scale, the concentrated reaction mixture was filtered through a glass frit with a layer of Magnesol (top layer, 40 g) and silica gel (bottom layer, 30 g) and the filter cake was washed with 20% EtOAc/hexanes (500 mL). The filtrate was concentrated in vacuo to afford 9.3 g of the product as a pale yellow oil (69% yield, 0.103% pure by quantitative NMR as described above).

Preparation of 2,5-dihydrothiophene-3,4-dicarboxylic acid

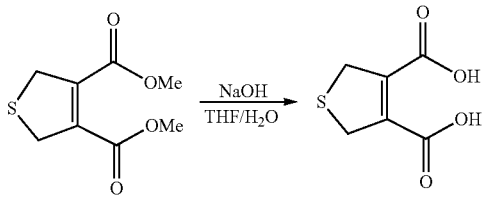

To a solution of dimethyl 2,5-dihydrothiophene-3,4-dicarboxylate (13.05 g, 45.17 mmol; Purity=70%) in THF (60 mL) was added 6 M sodium hydroxide in water (40 mL, 250.0 mmol). After an induction period (~10 min), there was an apparent exotherm (not measured). After 2.5 h, HPLC analysis showed complete conversion to diacid. The reaction mixture was concentrated in vacuo to remove THF. The mixture was diluted with TBME (100 mL), the layers were partitioned in a separator) funnel, and the organic layer was set aside. The aqueous layer was returned to the reaction flask and acidified with 2 M HCl (45 mL) to pH 1. A precipitate formed and was filtered (0.9 g). $^1$H NMR analysis of the precipitate was consistent with the diacid. The aqueous layer was extracted with EtOAc (3×100 mL). Combined extracts were dried over $Na_2SO_4$, filtered and concentrated in vacuo to afford the product (7.36 g; Yield=76.7%; Purity=82%) as a light orange solid. $^1$H NMR was acquired in DMSO-d6 w/p-xylene as an internal standard. When the reaction was run on a smaller scale (2.31 g; 72% purity), it afforded 1.2 g of the title compound at 92% purity (76% yield) as a tan-colored solid. When the reaction is run by adding diester to a NaOH solution, the exotherm is more easily controlled, but this led to a lower isolated yield (~50%) and the isolated product was less pure (60-75%).

Preparation of 4,6-dihydro-1H,3H-thieno[3,4-c]furan-1,3-dione

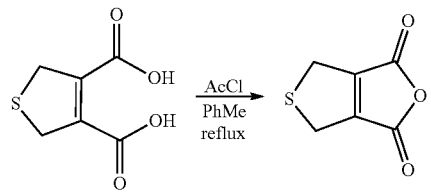 [SMILES: "AcCl" ; O=C(O)C1=C(C(=O)O)CSC1 ; O=C1OC(=O)C2=C1CSC2]

A suspension of 2,5-dihydrothiophene-3,4-dicarboxylic acid (1.22 g, 7.00 mmol) in toluene (4.9 mL, 46 mmol) and acetyl chloride (1.20 mL, 16.8 mmol) was heated to reflux for 4 h. The mixture was allowed to cool to rt and was concentrated in vacuo. The residue was suspended in acetone (10 mL) and was filtered through a pad of Magnesol (5 wts). The filter cake was washed with acetone (200 mL) and the filtrate was concentrated in vacuo to afford the product (0.801 g; Yield=70.3%; Purity=96%) as a tan solid.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of preparing a compound of Formula (I):

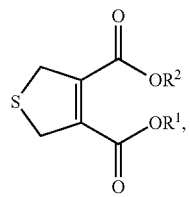

(I)

the method comprising reacting a compound of Formula (II):

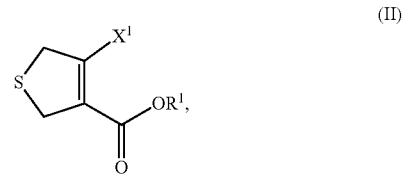

(II)

in the presence of palladium, carbon monoxide, and a reagent of the formula; $R^2OH$;
wherein:
$X^1$ is halogen, optionally substituted sulfonate, or optionally substituted phosphonate; and
$R^1$ and $R^2$ are independently optionally substituted alkyl, optionally substituted aryl, optionally substituted heteroaryl, optionally substituted carbocyclyl, optionally substituted heterocyclyl, or an oxygen protecting group.

2. The method of claim 1, wherein the palladium is a palladium salt.

3. The method of claim 1, wherein the palladium is palladium (II) or palladium (0).

4. The method of claim 1, wherein the palladium is palladium chloride ($PdCl_2$), palladium acetate ($Pd(OAc)_2$), palladium trifluoroacetate ($Pd(TFA)_2$), or tris (dibenzylideneacetone) dipalladium ($Pd_2(dba)_3$).

5. The method of claim 1, wherein the palladium is present in a catalytic amount relative to the compound of Formula (II).

6. The method of claim 1, wherein the step of reacting is carried out in the presence of a phosphine.

7. The method of claim 6, wherein the phosphine is triphenylphosphine ($Ph_3P$) or 1,1'-bis(diphenylphosphino) ferrocene (dppf).

8. The method of claim 6, wherein the phosphine is present in a catalytic amount relative to the compound of Formula (II).

9. The method of claim 1, wherein the step of reacting is carried out in a solvent.

10. The method of claim 9, wherein the solvent is a polar solvent.

11. The method of claim 1, wherein the step of reacting is carried out at around room temperature.

12. The method of claim 1, wherein $X^1$ is optionally substituted sulfonate.

13. The method of claim 12, wherein $X^1$ is mesylate ($—OSO_2CH_3$), tosylate ($—OSO_2C_6H_4p\text{-}CH_3$), or triflate ($—OSO_2CF_3$).

14. The method of claim 1, wherein $R^1$ and $R^2$ are the same.

15. The method of claim 1, wherein $R^1$ and $R^2$ are independently optionally substituted $C_{1-6}$ alkyl.

16. The method of claim 15, wherein $R^1$ and $R^2$ are independently methyl, ethyl, n-propyl, iso-propyl, n-butyl, iso-butyl, sec-butyl, or tert-butyl.

17. The method of claim 1, wherein $R^1$ and $R^2$ are methyl.

* * * * *